(12) United States Patent
Lohse et al.

(10) Patent No.: US 9,958,449 B2
(45) Date of Patent: *May 1, 2018

(54) METHOD FOR ENZYME-MEDIATED SIGNAL AMPLIFICATION

(71) Applicant: Dako Denmark A/S, Glostrup (DK)

(72) Inventors: Jesper Lohse, Herlev (DK); Galina Skladchikova, Hellerup (DK)

(73) Assignee: DAKO DENMARK A/S, Glostrup (DK)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/166,133

(22) Filed: May 26, 2016

(65) Prior Publication Data

US 2016/0274122 A1    Sep. 22, 2016

Related U.S. Application Data

(63) Continuation of application No. 14/112,808, filed as application No. PCT/DK2012/000049 on Apr. 19, 2012, now Pat. No. 9,366,675.

(60) Provisional application No. 61/556,917, filed on Nov. 8, 2011, provisional application No. 61/476,958, filed on Apr. 19, 2011.

(51) Int. Cl.
| | |
|---|---|
| *C12Q 1/26* | (2006.01) |
| *C12Q 1/28* | (2006.01) |
| *G01N 33/58* | (2006.01) |
| *G01N 33/574* | (2006.01) |

(52) U.S. Cl.
CPC ............. *G01N 33/581* (2013.01); *C12Q 1/26* (2013.01); *C12Q 1/28* (2013.01); *G01N 33/57492* (2013.01)

(58) Field of Classification Search
CPC ........... G01N 33/581; G01N 33/57492; G01N 33/00; C12Q 1/26; C12Q 1/28

USPC ............................. 435/7.92, 25, 28
See application file for complete search history.

(56) References Cited

U.S. PATENT DOCUMENTS

| | | |
|---|---|---|
| 5,863,748 A | 1/1999 | Bobrow |
| 7,173,241 B2 | 2/2007 | DiCesare |
| 8,435,735 B2 | 5/2013 | Lohse |
| 2004/0094705 A1 | 5/2004 | Wood et al. |
| 2006/0051831 A1 | 3/2006 | Matsuo et al. |
| 2012/0163681 A1 | 6/2012 | Lohse et al. |
| 2012/0270242 A1 | 10/2012 | Lohse |

FOREIGN PATENT DOCUMENTS

| | | | |
|---|---|---|---|
| CN | 101836117 A | 9/2010 | |
| CN | 102713626 A | 10/2012 | |
| EP | 2491390 B1 | 3/2014 | |
| WO | 9826095 A1 | 6/1998 | |
| WO | 2009036760 A2 | 3/2009 | |
| WO | WO2010094283 * | 8/2010 | ............ C12Q 1/28 |
| WO | 2011047680 A1 | 4/2011 | |
| WO | 2012062318 A1 | 5/2012 | |

OTHER PUBLICATIONS

International Search Report for PCT/DK2012/000049, dated May 9, 2012.
European Search Report for Application No. 12 721 746.1-1404 dated Sep. 11, 2015.
Chinese Office Action for 201280029392.3, dated Dec. 8, 2015.

* cited by examiner

*Primary Examiner* — Scott Long
*Assistant Examiner* — Paul C Martin

(57) ABSTRACT

The present invention relates to methods and compounds for enzyme-mediated amplification of target-associated signals for visualization of biological or chemical targets in samples, wherein the targets are immobilized, in particular the invention relates to the oxidoreductase-mediated signal amplification for visualization of targets in samples comprising cells. The methods of the invention are particular useful for qualitative and quantitative evaluation of biological markers relating to medical diagnostic and therapy.

15 Claims, No Drawings

US 9,958,449 B2

METHOD FOR ENZYME-MEDIATED SIGNAL AMPLIFICATION

CROSS-REFERENCE TO RELATED APPLICATIONS

This application is a continuation of U.S. application Ser. No. 14/112,808, filed Dec. 24, 2013, now U.S. Pat. No. 9,366,675, issued Jun. 14, 2016, which is a national stage filing under 35 U.S.C. § 371 of International Application No. PCT/DK2012/000049, filed Apr. 19, 2012 and designating the United States of America, which claims benefit of the filing date of and right of priority to U.S. Provisional Application No. 61/556,917, filed Nov. 8, 2011, and U.S. Provisional Application No. 61/476,958, filed Apr. 19, 2011, all of which are incorporated herein by reference.

FIELD OF THE INVENTION

The present invention relates to methods and compounds for enzyme-mediated amplification of target-associated signals for visualization of biological or chemical targets in samples, wherein the targets are immobilized. The methods of the invention are useful for qualitative and quantitative evaluation of biological markers in histological samples, in particular in diagnostic applications.

BACKGROUND OF THE INVENTION

Immunochemistry (IHC) is a common tool in medical diagnostics and it is also usual for the assessment of therapeutic biomarkers. The latter, in particular, often require a quantitative evaluation of the extent of their presence. The application of antibodies to cells and tissues presents specific difficulties beyond those encountered when these reagents are applied to purified proteins immobilized onto solid supports in or solution. There are many factors that can affect immunodetection, among these fixation and preparation of tissue, duration and type of antigen retrieval and antibody specificity. An additional difficulty is the ability to detect targets present at low levels. In common with soluble assays, this becomes a matter of increasing signal without raising the level of nonspecific background. The approach that has been most commonly explored is signal amplification, which is achieved by successive rounds of enzymatic reactions.

3,3'-Diaminobenzidine (DAB) is a chromogeninc substrate of horse radish peroxidase (HRP) that is widely used for visualizing of target proteins in histological samples which are labeled with peroxidase activity. The method utilizes HRP linked to antibodies targeted to proteins of a sample that deposits DAB from a solution to the sites of targeted proteins and thereby labels the proteins. The method is not especially sensitive and therefore suitable for detection of relatively abundant target proteins. The signal associated with DAB deposits cannot be further amplified. Other drawbacks to mention are that the method demands rather high amounts of target specific antibodies to saturate all target sites and it is relatively time consuming. Furthermore, the method provides a uniform staining pattern that appears to the microscopist as a homogeneous color with intracellular resolution of cellular structures, e.g. membrane, cytoplasm, and nucleus, which makes it impossible to quantify the staining accurately.

Recently, a novel HRP-DAB-based IHC visualization system has been described. This system utilizes DAB not only as a chromogenic substrate of HRP to label targets, but also as an agent which cross-links other detectable HRP substrates in aqueous solutions with the assistance of HRP and deposits them thereby in the vicinity of the immobilized HRP (see WO2009036760, WO2010094283 and WO2010094284). In histological samples the method produces a staining pattern that is similar to a traditional HRP-DAB staining, but, compared to the traditional staining, this staining is much more target specific and sensitive and the procedure is much faster and robust.

The new method does not allow direct approximating the quantity of the target to the quantity of the stain in a sample, because the correlation between these two quantities is not linear. Accordingly, the quantity of a target in a histological sample visualized by all these methods can only be assessed relatively, not precisely. However, under certain conditions, this newly described HRP-DAB target labeling system is capable of amplifying a signal associated with a single target so strongly, that that single targets, such as single protein or nucleic acid molecules, may be visualized in the samples individually as large dots of color or fluorescence and detected by using ordinary low magnification bright-field or fluorescence optics (see WO2011047680). The visually distinct single dots with a diameter up to 4 microns may be then easily manually or automatically quantified in the sample and the amount of the target may be determined very precisely (see PCT/DK 2011/000131).

SUMMARY OF THE INVENTION

This invention relates to a novel powerful signal amplification system applicable to samples where the targets are immobilized, e.g. onto or within solid supports, that makes possible visualizing individual single entities of targets, such as single biological or chemical molecules, single molecular structures, single molecular complexes, single particles etc., in a very wide dynamic concentration range in a host variety of samples either as visually distinct dots of an apparent diameter of around 1 to around-3 microns. The system is also applicable for visualizing an immobilized target in as a homogeneous stain (i.e. without resolution into evident single dots).

An amplification system according to the invention comprises at least one step of incubating of a sample supposedly comprising a target in an aqueous solution comprising:

i) a first substrate of an enzyme with oxidoreductase activity;

ii) a second substrate of said enzyme, and, optionally, iii) a peroxide compound, wherein the first substrate is alpha-cyano-4-hydroxycinnamic acid (ACHCA) or a derivative thereof and the second substrate is a conjugate molecule comprising one or more compounds that are capable of serving as substrates of the enzyme with oxidoreductase activity and a detectable label.

According to the invention, incubating of the sample supposedly comprising a target in the above aqueous solution results in labeling sites of the sample that comprises that target with deposits of the conjugate molecules, however, only in cases if the target comprises an oxidoreductase activity, and the target is immobilized within the sample, or immobilized onto or within a solid support. An immobilized target may comprise oxidoreductase activity inherently or it may be associated with the enzyme through another substance, e.g. the target specific binding agent that comprises horse radish peroxidase (HRP) or soybean peroxidase (SP). The target in the sample is detected by means of detecting a detectable label of the deposited second substrate.

Accordingly, in some embodiments, a method of the invention may comprise steps:
  a) Incubating a sample supposedly comprising an immobilized target comprising an enzyme with oxidoreductase activity, in an aqueous solution comprising:
    (i) a first substrate of said enzyme;
    (ii) a second substrate of said enzyme, and, optionally,
    (iii) a peroxide compound,
  wherein the first substrate is alpha-cyano-4-hydroxycinnamic acid (ACHCA) or a derivative thereof and the second substrate is a conjugate molecule comprising one or more compounds that are capable of serving as substrates of the enzyme with oxidoreductase activity and a detectable label;
  b) Detecting the label of the deposited molecules of second substrate in the sample.

In other embodiments, a method of the invention may comprise steps:
  a) Incubating a sample supposedly comprising a target, wherein the sample or the target is immobilized, with one or more binding agents, wherein at least one of the binding agents is the target specific binding agent, and at least one of the binding agents comprises an enzyme with oxidoreductase activity;
  b) Incubating the sample (a) in an aqueous solution comprising:
    (i) a first substrate of said enzyme;
    (ii) a second substrate of said enzyme, and, optionally,
    (iii) a peroxide compound,
  wherein the first substrate is alpha-cyano-4-hydroxycinnamic acid (ACHCA) or a derivative thereof and the second substrate is a conjugate molecule comprising one or more compounds that are capable of serving as substrates of the enzyme with oxidoreductase activity and a detectable label;
  c) Detecting the label of the deposited molecules of second substrate in the sample.

The term "optionally" means that the peroxide compound is not an essential component of the aqueous solution in all embodiments of the invention: it is a component of the solution, when the enzyme with oxidoreductase activity is a peroxidase, and it may be avoided from the solution when the enzyme is a phenoloxidase.

In other embodiments, methods of the invention may comprise one or more further detection steps including additional signal amplification steps using the amplification system according to the present invention or using other amplification systems, e.g. the amplification system of WO2011047680, WO2009036760, WO2010094283 or WO2010094284.

Target visualization methods utilizing the amplification system of the invention are suitable for both (i) visualization of single entities of targets in samples where the target is immobilized as distinct dots of stain (or fluorescence or radioactivity), wherein a single dot has an apparent diameter of between around 1 and around 3 microns and corresponds to a single unit of the target, and (ii) visualizing target as homogeneous stain (i.e. does not consist of multiple distinct dots of stain such as dots of a diameter 1 to 3 microns).

The visualization system of the invention allows detecting multiple and diverse targets in one sample using diverse combinations of the target-specific binding agents, a plurality of different detectable labels, combinations of different signal amplification systems, a plurality of enzyme substrates, etc.

One aspect of the invention relates to quantification of the target visualized according to present invention. Both single target entities and total amount of the target in the sample may be quantified very precisely.

Another aspect of the invention relates to use of the amplification system in medical diagnostic as part of a diagnostic assay. Sensitivity and precision of detection of diagnostic targets and quantification by the methods of the invention is a great asset to molecular and companion diagnostics and personalized therapy.

Additional advantage of the visualization system of the invention is that it uses compounds that are (i) non-toxic, (ii) colorless (iii) well-defined, (iv) stable and (v) easily obtainable.

A further advantage is that all methods of the invention can be carried out both manually and automatically.

DETAILED DESCRIPTION OF THE INVENTION

The present invention relates to a powerful signal amplification system that is usable for visualization and detection of an immobilized target, e.g. onto a support, in a variety of samples using a variety of assay formats, wherein the target comprises oxidoreductase enzymatic activity. The amplification system of the invention is, in particular, advantageous for the detection of target biological molecules in complex histological samples.

A target visualization system according to the invention comprises at least one step of incubating of a target supposedly comprising oxidoreductase activity, wherein the target is immobilized onto a support, in an aqueous solution comprising:
  i) a first substrate of the enzyme with oxidoreductase activity associated with the target;
  ii) a second-substrate of said enzyme, and, optionally,
  iii) a peroxide compound,
wherein
the first substrate is alpha-cyano-4-hydroxycinnamic acid (ACHCA) or a derivative thereof, and
the second substrate is a conjugate molecule comprising one or more compounds that are capable of serving as substrates of the enzyme with oxidoreductase activity and a detectable label.

In one embodiment, the invention relates to a method for detecting a target supposedly comprising oxidoreductase activity in a sample, wherein the target and/or sample is immobilized, that comprises steps:
  a) Incubating the sample supposedly comprising the target in an aqueous solution comprising:
    (i) a first substrate of an enzyme with oxidoreductase activity
    (ii) a second substrate of said enzyme, and, optionally,
    (iii) a peroxide compound,
  wherein the first substrate is alpha-cyano-4-hydroxycinnamic acid (ACHCA), or a derivative thereof, and the second substrate is a conjugate molecule comprising one or more compounds that are capable of serving as substrates of the enzyme with oxidoreductase activity and a detectable label;
  b) Detecting the label of the deposited molecules of second substrate in the sample.

In another embodiment, a method for detecting a target in a sample, wherein the target and/or sample is immobilized, that comprises steps:
  a) Incubating the sample supposedly comprising the target with one or more binding agents, wherein at least one of the binding agents is the target specific binding agent and at least one of the binding agents comprises an enzyme with oxidoreductase activity;
b) Incubating the sample (a) in an aqueous solution comprising:
   (i) a first substrate of said enzyme;
   (ii) a second substrate of said enzyme, and, optionally,
   (iii) a peroxide compound,
wherein the first substrate is alpha-cyano-4-hydroxycinnamic acid (ACHCA) or a derivative thereof, and the second substrate is a conjugate molecule comprising one or more compounds that are capable of serving as substrates of the enzyme with oxidoreductase activity and a detectable label;
c) Detecting the label of the deposited molecules of second substrate in the sample.

In different embodiments, methods of the invention may comprise one or more additional steps, e.g. washing steps, further target detection steps, additional signal amplification steps, e.g. signal amplification steps according to the present invention or to other amplification systems, e.g. the amplification system described in WO2011047680 or steps of the Rolling Circle Amplification (RCA) system, steps of visualization other targets using one of the methods described in the art, e.g. H&E staining, Alkaline Phosphatase (AP)-based staining, etc. The amplification system described herein may be combined with virtually any signal amplification system applicable developed in art for visualization of immobilized molecular targets.

Different aspects and non-limiting embodiments of the signal amplification system and target visualization and detection methods of the invention are described below.

Sample

The term "sample" means a representative part or a single item from a larger whole or group, an amount or portion of a matter or object that supposedly contain a target to be detected, e.g. a portion or amount of biological, chemical, environmental material comprising a target molecule, particle, structure to be analyzed, e.g. a biopsy sample, a food sample, a soil sample, etc. A typical sample shows what the rest of the matter or object is or should be like. In one embodiment a sample of the invention may be an environmental sample, e.g. a sample of a soil or a sample of a spillage. In another embodiment the sample may be a food sample. In another embodiment the sample may be a portion of a library of organic molecules. In another embodiment the sample may be a sample of warfare.

In one embodiment a sample of the invention is a biological sample.

A biological sample may be exemplified by:
1. a sample comprising suspended cells and/or cells debris, e.g. blood sample, suspension of cloned cells, body tissue homogenate, etc;
2. a sample comprising of intact or damaged cells of an animal body, a body tissue, smear or fluid or a sample of a tumor, e.g. a biopsy sample; It may be a fresh tissue sample or preserved tissue sample, e.g. a formalin fixed paraffin embedded tissue sample;
3. a sample comprising a living organism, e.g. a sample of a medium comprising an animal, plant, bacterium, fungi, etc;
4. a sample comprising viral particles, debris thereof, or viral products, e.g., a body smear comprising viral nucleic acids, proteins, peptides, etc;
5. a sample comprising a cell organelle(s);
6. a sample comprising natural or recombinant biological molecules, e.g. blood plasma sample, conditioned cell culture media, etc.
7. a sample comprising plant cells or derbies thereof.

The above mentioned examples of biological samples are given for the purpose of illustration, but not limitation of embodiments of the invention.

Examples of chemical samples may be illustrated by and are not limited to samples of libraries of chemical compounds, e.g. peptide libraries. Examples of the environmental samples may be illustrated by and are not limited to soil, water or air samples and food samples.

In some embodiments the invention relates to samples (e.g. as any of the above examples) comprising an immobilized target, i.e. to samples where the target is prevented from freedom of movement during a visualization and detection procedure according to the present invention, e.g. samples where the target motion is substantially reduced or eliminated by mechanical or chemical means, as e.g. in case of samples or targets attached to or within a certain support or medium, e.g. histological samples or the like. Thus, a sample comprising single and/or aggregated individual units of a target of interest may be immobilized onto a solid support before the detection procedure. Examples of samples comprising immobilized targets of the invention include but not limited to fresh or archive (e.g. formalin fixed and paraffin embedded) biological tissue samples immobilized onto surfaces of glass or plastic slides, samples comprising biological or chemical molecules immobilized onto membranes, ELISA plates, or the like. A target of a sample in these embodiments may be immobilized either within the sample, e.g. a protein fixed within a tissue sample, or is immobilized on the surface or within certain material, such as e.g. a portion of a solid material or a gel such as a nitrocellulose membrane, collagen/agarose/paraffin block, etc.

In one embodiment the invention relates to a sample that does not comprise the target, e.g. a control sample. In another embodiment, the invention relate to a sample that supposedly comprise the target, e.g. a sample with unknown content.

The term "solid support" mentioned above means a piece of any material that is solid and chemically inert under conditions of the procedures according to the invention. "Chemically inert" means in the present context that the chosen support has a minimal or no influence at all on the results of target visualization and detection by the methods of the invention.

Examples of materials suitable for supports for immobilizing samples/targets of the invention include but not limited to synthetic polymer supports, such as polystyrene, polypropylene, substituted polystyrene, e.g, aminated or carboxylated polystyrene; polyacrylamides; polyamides; polyvinylchloride; glass; agarose; nitrocellulose; nylon; polyvinylidenedifluoride; surface-modified nylon, etc. Any such inert support suitable for immobilizing a sample or target and suitable for the chosen assay format, e.g. for IHC, ELISA, blotting etc, may be selected.

Target

The term "target" means in the present content an object of interest supposedly present in a sample that can be characterized by particular physical and/or functional features. If it is not expressly specified in the context, the term "target" according to the invention relates to the whole pool of substantially identical entities of an object of interest in a sample, not to one single entity of that object. The term "substantially identical" in the present context means that all or substantially all single entities of the total pool of a target in a sample possess one or more features that make them recognizable as the target, for example, the target may be a particular protein (including all molecules of that particular protein in the sample), a particular molecular complex or structure (including substantially all units of that particular molecular complex or molecular structure in the sample), it may be a virus or bacterium, wherein total population of the viral particles or bacterial bodies of the sample is the target.

Biological objects, such as molecules, molecular complexes, structures, particles or organisms, which are associated with features that are characteristic for a particular cell type, tissue, cellular structure, physiological condition, etc., are often referred in the art as "biological markers" of that particular cell type, tissue, cellular structure, or physiological condition. Non-limited examples of such biological markers that may in different embodiments be targets of the present invention include but not-limited to nucleotide sequences, proteins or other biological molecules, e.g. carbohydrates or lipids, chromosomal or membrane structures, viruses, bacteria, microorganisms etc. In some embodiments of the invention, the term "target" is thus used interchangeable with the term "biological marker" and relates to a molecule, molecular complex, structure or particle that is characteristic for a particular cell type, tissue, physiologic condition, etc, wherein the total population of any of the latter biological markers in the test sample is considered to be the target.

In one embodiment, the target may be a protein, e.g. a cellular membrane receptor or a cytoplasmic protein, in another embodiment the target may be a nucleic acid, e.g. a cytoplasmic nucleic acid. Derivatives of any latter mentioned targets, including fragments, precursors, mutants, etc. may also be targets in some embodiments of the invention.

Thus, in different embodiments of the invention the target may be a biological or chemical target molecule, or a particle, or a molecular or cellular complex, or molecular or cellular structure, or a virus, or a microorganism, or a fragment of said target molecule, particle, complex, structure, virus or microorganism. Among targets contained in chemical and environmental samples may be different pollutants, toxins, warfare substances, members of molecular libraries, industrial noxious waste compounds, etc.

In one embodiment the invention relates to a target that is a plurality of individual substantially identical units. By the term "unit" is meant a single quantity of a target regarded as a whole in calculation that can be identified by physical and/or functional features that define the target. The term "individual unit" means that a unit is separable from the other units of the same kind or other components of the environment (by physical features of a function) and can be considered and counted separately. The term "single unit" in the present content means that one target unit, i.e. one as opposed to or in contrast with many. The term "individual unit" is interchangeably used herein with the term "single unit". For example, a single/individual unit of a target protein means in the present context a single individual molecule of the target protein, i.e. one molecule of plurality molecules of the same kind. The term "substantially identical units" means that a plurality of single units of a target possesses one or more features that make these units be considered as the target. The term "independent" means that a single unit of a target exists as a distinct entity and do not depend on the existence of other distinct entities of the same kind in the sample.

In one embodiment, the invention relates to single units of a target, e.g. single target molecules, single particles, or the like.

The invention in some embodiments relates to a single target unit being a part of a biological molecule that has particular physical or functional properties that allow considering this part of the molecule separately from the other parts of the same molecule, e.g. a proteolytic fragment of a target protein, a part of a fusion protein, a particular domain of a target protein, a particular structure of a nucleic acid, an epitope, etc.

In different embodiments a plurality of single units of a target may be represented by single individual biological or chemical molecules, single individual single particles, single individual molecular or cellular complexes, single individual molecular or cellular structures, or single individual viruses or single individual microorganisms, or single individual fragments of said molecules, particles, complexes, structures viruses or microorganisms.

In one preferred embodiment, the target is a biological marker related to cancer, e.g. nucleic acids and polypeptides of hormones and growth factors and their receptors, cell adhesion molecules signal transduction molecules, cell cycle regulation molecules, etc, e.g. genes, RNAs and proteins of the group including growth factors PDGF, VEGF, TGF, HGF or EGF, their receptors and the pathway related molecules, genes and their products relating to signal transduction pathways, e.g. the JAK/STAT pathway or Akt1/PKB cell survival pathway, or 5-FU pathway, estrogen receptor ER and its gene (ERS1), etc. The methods of the invention allow simple and rapid visualization and quantification of said biological markers.

Methods of the invention allow visualizing and quantifying a target present in a sample in a broad dynamic range. Both very high amounts and very low amounts of a target may be visualized and quantified in one and the same sample, or they may be evaluated in separate samples. Two or more different targets may be visualized in one or the same sample, e.g. a protein target and nucleic acid target, or two or more different protein targets, or two or more different nucleic acid targets, etc.

In one embodiment, single units of a target may be distributed substantially homogeneously throughout a sample, in other embodiments, single units of a target may present more abundant in one part of a sample and less abundant in other parts thereof. In all the latter embodiments, single units of the target may be visualized and quantified in one and the same sample using methods of the present invention. In some embodiments, wherein one target of interest is associated with another target of interest, e.g. the first and second targets are present in a sample in a particular molecular association or structure, e.g. a receptor dimer, the another target of interest may be visualized and quantified either by visualizing and quantifying the first target in the sample, or two such targets may be visualized and quantified independently.

In some embodiments the invention may relate to a fractional sub-population of single units of a target, such as a major or a minor portion of the total number of single individual units of the target present in the sample. The term "fractional subpopulation" in the present context means a portion of the total population of single target units that is equal or less than 99%. e.g. equal or less than 90% of the total quantity of single units of the target in the sample, such as less than 85%, e.g. 75-80% of the total quantity of units of the target in the sample, such as less than 75%, for example from 1% to 50% of the total quantity of single units of the target in the sample, such as from 1% to 25% of the total quantity of units of the target in the sample, etc. A fractional sub-population single target units that is represented by 50%-99% of the total population is defined according to the invention as a majority of single target units present in the sample. A fractional sub-population is represented by less than 50% of the total population of single target units in a sample is defined according to the invention as a minority of single target units present in the sample.

In one embodiment, a majority of individual single target units may be involved in formation of discrete single target sites of the invention; in another embodiment, a minority of individual single target units may be involved in formation of discrete single target sites of the invention. In one embodiment, when a target or single units of a target are present in a sample in very low amounts, it may be preferred that substantially all individual single units are involved in formation of single binding sites of the invention. A single binding site of the invention is a site of a sample or a support comprising an immobilized target that inherently comprises an oxidoreductase enzymatic activity or is associated with an agent that comprises said enzymatic activity.

In one embodiment, the target may be a molecule, structure, particle, microorganism (or the like) that has inherent oxidoreductase enzymatic activity, e.g. a peroxidase enzyme such as HRP or the like. In another embodiment, a target may be a compound, molecule, structure, particle, microorganism (or the like) that does not have said enzymatic activity. In the latter embodiments, the target according to the invention may be labeled with said enzymatic activity, e.g. with help of a binding agent that comprises an oxidoreductase activity.

Binding Agent

In some embodiments, target visualization methods of the invention may comprise a step wherein a sample presumably comprising a target is incubated with one or more binding agents, wherein (i) at least one thereof is capable of recognizing and specifically binding to the target, and (ii) at least one thereof comprises oxidoreductase activity.

The term "binding agent" means in the present context a molecule or another substance, e.g. a particle, that is capable of directly and specifically binding to its binding partner in the sample, e.g. to a target molecule, another binding agent, hapten, etc. The term "specifically" means that the binding agent has a particular affinity to its binding partner. The term "directly" means that the binding agent interacts and forms an immediate bond with its specific binding partner upon interaction. As contrary, the term "indirectly" in the present context relates to a specific interaction between two substances that do not have specific affinity to each other, and their interaction is mediated by other agents, wherein at least two of said agents are members of a specific binding pair. One example illustrating an indirect binding of the invention may be a complex comprising a target protein molecule, a primary antibody bound to the target protein and a secondary antibody bound to the primary antibody. In the latter complex the secondary antibody is according to the invention interects to the target protein indirectly.

A binding agent which is capable of directly and specifically binding to a target in the sample is termed herein "first binding agent"; a binding agent which is capable of directly and specifically binding to the first binding agent or to a substance directly associated with the target, is termed herein "second binding agent". A target visualization system according to the invention may comprise a number of binding agents that may be indirectly bound to the target, e.g. third, fourth, and further binding agents. In some embodiments, a first binding agent or, in other embodiments, a second or third binding agent, may be used to contact a sample to recognize the target, bind to it and form a complex with it. In some embodiments, the first or second binding agent may comprise an enzymatic activity according to the invention and be used to label the target with this enzymatic activity. Third and further binding agents may also comprise an enzymatic activity and be used in further steps of methods according to the invention, e.g. detection the deposits of detectable conjugate molecules at target sites, etc. In some embodiments, second, third and further binding agents are used to amplify, change or reduce a signal associated with the target.

Binding agents of the invention in preferred embodiments are members of different specific binding pairs.

A number of different specific binding pairs are known in the art, these are the pairs of two different molecules which are capable of specific binding to each other. Members of specific binding pairs suitable for use in practicing the invention may be of the immune or non-immune type.

Non-immune specific binding pairs include systems wherein the two components share a natural affinity for each other but are not antibodies. Exemplary non-immune binding pairs are biotin-avidin or biotin-streptavidin, folic acid-folate binding protein, complementary nucleic acids, receptor-ligand, etc. The invention also includes non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler dyes such as 3-methyl-2-benzothiazolinone hydrazone (MBTH) and 3-(dimethyl-amino)benzoic acid (DMAB), etc.

Immune specific binding pairs may be exemplified by antibody-antibody systems or hapten-anti-hapten systems. In one embodiment the immune specific binding pair of the invention may be an antibody-antibody binding pair comprising two or more antibody molecules having affinity to each other, for example a primary antibody and secondary antibody pair, wherein the primary antibody represents the first binding agent and the secondary antibody represents the second binding agent; Antibody systems comprising 3 or 4, or more antibody members may be used in another embodiment. In other embodiments of the invention the immune binding pair may be represented by a hapten-anti-hapten system. In such embodiments the first binding agent may be represented by a conjugate comprising a molecule having affinity to the target and a hapten, e.g. a primary antibody or nucleic acid sequence linked to a hapten, and the second binding agent may be represented by an anti-hapten antibody.

The term "hapten" designates a small molecule which can be considered as an isolated epitope to which an antibody can be made, although the hapten alone will not induce an immune response if injected into an animal, it must be conjugated to a carrier (usually a protein). As haptens are small molecules, multiple copies of a hapten may be attached to a large molecule, e.g. a polymer molecule, such as protein, nucleotide sequence, dextran, etc. Haptens may serve as convenient label molecules for assay formats where it is necessary or advantageous to amplify a signal. Thus, the bound multiple copies of a hapten provide for enhanced sensitivity, e.g. increased signal strength. Non-limited examples of suitable haptens include Fluorescein (FITC), 2,4-Dinitrophenol (DNP), myc Digoxigenin (DIG), tyrosine, nitrotyrosine biotin and dyes. e.g. tetramethylrhodamine, Texas Red, dansyl, Alexa Fluor 488, BODIPY FL, lucifer yellow and Alexa Fluor 405/Cascade Blue fluorophores, Haptens are described in US20080305497 may also be used for the purposes of the invention.

The term "antibody", as used herein, designates an immunoglobulin or a part thereof, and includes any polypeptide comprising an antigen binding site regardless of the source, method of production, and other characteristics. The term includes for example, polyclonal, monoclonal, monospecific, polyspecific, humanized, single chain, chimeric, synthetic, recombinant, hybrid, mutated, and CDR-grafted antibodies. A part of an antibody can include any fragment which can still bind antigen, for example, an Fab, F(ab')$_2$, Fv, scFv. The origin of the antibody is defined by the genomic sequence irrespective of the method of production.

Primary antibody, in context of the present invention, refers to an antibody binding agent, e.g. a whole antibody molecule, a fragment or a derivative of said molecule, e.g. a conjugate comprising an antibody or a polymerized antibody, that specifically binds to a target, more specifically to a single unit of a target of a sample, e.g. to a single target molecule. In some embodiments, a primary antibody may be a bivalent antibody which is capable of binding to two (or more) single individual units of different targets, e.g. an antibody that is capable of binding to a receptor dimer, e.g. Her2/Her3 dimer. In this embodiment the single unit of a target according to the invention is a single Her2/Her3 dimer, and the target is a population of Her2/her3 dimers in a sample including all said dimers of the sample. Primary antibodies may be derived from any warm blooded species, e.g. mammals, birds.

Secondary antibody, in context of the present invention, refers to an antibody binding agent, e.g. a whole antibody molecule, a fragment or a derivative of said molecule, e.g. a conjugate comprising an antibody or a polymerized antibody, that has an antigen binding domain that specifically binds to the primary antibody, or a hapten deposited in the target site, or a hapten linked directly or indirectly to a primary antibody or another binding agent.

Tertiary antibody, in context of the present invention, refers to an antibody binging agent, e.g. a whole antibody molecule, a fragment or a derivative of said molecule, e.g. a conjugate comprising an antibody or a polymerized antibody that comprise an antigen binding domain that specifically binds to a secondary antibody or a hapten linked to a secondary antibody or a hapten linked to polymer conjugated to a secondary antibody, or a hapten of the conjugate molecule deposited at a target site.

Sometimes an antibody may function both as a secondary and a tertiary antibody.

Antibodies used in the invention, including primary antibodies, secondary antibodies and tertiary antibodies, may be derived from any mammal species, e.g., a rat, a mouse, a goat, a guinea pig, a donkey, a rabbit, horse, lama, camel, or any avian species e.g., chicken, duck. Derived from any mammal or avian species, as used herein, means that at least a part of the nucleic acid sequence encoding a particular antibody originated from the genomic sequence of a specific mammal, e.g., a rat, a mouse, a goat, or a rabbit or a specific bird e.g., chicken, duck. The antibody may be of any isotype, e.g., IgG, IgM, IgA, IgD, IgE or any subclass, e.g., IgG1, IgG2, IgG3, IgG4.

In certain embodiments a primary antibody contains an antigen binding region which can specifically bind to a biological marker, in particular to a single individual unit of said biological marker, expressed by cells of a biological sample. The marker may be expressed on the cell surface or within the cell membrane, i.e., on the interior of the cell, e.g., within the cytoplasm, within the endoplasmic reticulum, etc. In some embodiments the biological marker may be extracted from the cell and thus it is present in a cell-free medium, e.g. in an aqueous solution, or it is a soluble molecule present in a cell culture media, blood plasma, cerebrospinal fluid, etc. Examples of the corresponding samples are described above.

In certain embodiments, a secondary antibody contains an antigen binding region which specifically binds to a primary antibody, e.g., to the constant region of the primary antibody. In certain embodiments, a secondary antibody may be conjugated to a polymer. In some embodiments, 2-20 secondary antibodies, such as 5-15 secondary antibodies may be conjugated with a polymer. In other embodiments, a polymer may be conjugated with 1-10 secondary antibodies, such as 1, 2, 3, 4, 5, 6, 7, 8, 9 or 10 secondary antibodies.

In certain embodiments, a tertiary antibody may contain an antigen binding region which specifically binds to a secondary antibody, e.g., to a constant region of a secondary antibody, or to a hapten linked to a secondary antibody, or to a polymer conjugated with a secondary antibody. In certain embodiments, a tertiary antibody is conjugated to a polymer. In some embodiments, 1-20 tertiary antibodies may be conjugated a polymer. In other embodiments, 1-5 tertiary antibodies, such as 1, 2, 3, 4 or 5 tertiary antibodies may be conjugated with a polymer.

In some embodiments, polymers comprising a single binding unit of a binding agent, e.g. a polymer conjugated with one molecule of primary, secondary or tertiary antibody, may be preferred.

Antibodies that may be used for the purposes of the invention include monoclonal and polyclonal antibodies, engineered antibodies including chimeric, CDR-grafted and artificially selected antibodies produced using phage display or alternative techniques.

Antibody binding agents of the invention may be produced by any of numerous methods well-known in the art e.g., according to Harlow and Lane, *Antibodies: a Laboratory Manual*, (1988) (Cold Spring Harbor Press, Cold Spring Harbor, N.Y.). Techniques for the preparation of recombinant antibody molecules are described in the above reference and a number of other references, e.g., EP 0623679; EP 0368684; and EP 0436597. Nucleic acids encoding antibodies may be isolated from a cDNA library. Nucleic acids encoding antibodies may be isolated from a phage library (see e.g. McCafferty et al. 1990, *Nature* 348:552, Kang et al. 1991, *Proc. Natl. Acad. Sci. USA* 88:4363; EP 0 589 877 B1). Nucleic acids encoding antibodies can be obtained by gene shuffling of known sequences (Mark et al. 1992, *Bio/Technol.* 10:779). Nucleic acids encoding antibodies can be isolated by in vivo recombination (Waterhouse et al. 1993, *Nucl. Acid Res.* 21:2265). The antibodies used in the methods of the invention include humanized immunoglobulins (see U.S. Pat. No. 5,585,089, Jones et al. 1986, *Nature* 332:323). Antibodies of the invention may be altered any possible way, presuming that they retain their binding affinity, e. g, they may fused with an effector protein, toxin, label, etc. Methods of conjugation of antibody with different agents are also well known in the and described in exemplary embodiment of the invention below.

In one embodiment of the invention, an antibody binding agent is represented by the Fab region.

In one embodiment an antibody binding agent may be a composition comprising two or more different antibody binding agents, e.g., a composition comprising a first antibody binding agent and a second antibody binding agent, wherein the two or more different antibody binding agents are of different immune binding pairs. In one embodiment, in the composition, at least one of two or more different antibody binding agents of is an antibody that is capable of specifically binding to a target and at least one another is an antibody which comprises a an enzyme.

In another embodiment, the invention relates to binding agents that are members of non-immune specific binding pairs, such as complementary nucleotide sequences, or nucleic acid analog molecules.

A binding agent comprising a nucleic acid or nucleic acid analog molecule, e.g., a DNA molecule, an RNA molecule, a PNA molecule, may be useful for the visualization and quantification of single individual units of nucleic acid targets.

Nucleic acid sequences used as binding agents for the purposes of the invention may be synthesized chemically or produced in recombinant cells. Both modes of production are well known in the art (see e.g. Sambrook et al. (1989) *Molecular Cloning: A Laboratory Manual, 2nd ed.* Cold Spring Harbor Press). In some embodiments, a nucleic acid binding agent may comprise a peptide nucleic acid (PNA). A peptide nucleic acid is a nucleic acid molecule in which the deoxyribose or ribose sugar backbone, usually present in DNA and RNA is replaced with a peptide backbone. Methods of making PNAs are known in the art (see e.g. Nielson, 2001, *Current Opinion in Biotechnology* 12:16) (hereby incorporated by reference). In other embodiments, the binding agent may comprise a locked nucleic acid (LNA) (Sorenson et al. 2003, *Chem. Commun.* 7(17):2130).

A nucleic acid binding agent, in some embodiments, may comprise at least one oligo- or at least one polynucleotide sequence that specifically hybridizes to a single unit of a target sequence in a biological sample, e.g. a single mRNA sequence, under specific conditions of stringency. The term "hybridization under stringent conditions," is used herein to describe conditions for hybridization under which nucleotide sequences that are significantly complementary to each other, such as at least 70%, at least 80%, at least 85-90% complementary, remain bound to each other. The percent complementary is determined as described in Altschul et al. (1997) *Nucleic Acids Res.* 25:3389-3402 (hereby incorporated by reference).

Specified conditions of stringency are known in the art and can be found in *Current Protocols in Molecular Biology*, John Wiley & Sons, Inc. (Ausubel et al. 1995 eds.), sections 2, 4, and 6 (hereby incorporated by reference). Additionally, specified stringent conditions are described in Sambrook et al. (1989) *Molecular Cloning: A Laboratory Manual, 2nd ed.* Cold Spring Harbor Press, chapters 7, 9, and 11 (hereby incorporated by reference). In some embodiments, the hybridization conditions are high stringency conditions. An example of high stringency hybridization conditions is hybridization in 4× sodium chloride/sodium citrate (SSC) at 65-70° C. or hybridization in 4×SSC plus 50% formamide at 42-50° C., followed by one or more washes in 1×SSC, at 65-70° C. It will be understood that additional reagents may be added to hybridization and/or wash buffers, e.g., blocking agents (BSA or salmon sperm DNA), detergents (SDS), chelating agents (EDTA), Ficoll, PVP, etc.

In some embodiments, the binding agents may hybridize to a target sequence in a sample under moderately stringent conditions. Moderate stringency, as used herein, include conditions that can be readily determined by those having ordinary skill in the art based on, for example, the length of the DNA. Exemplified conditions are set forth by Sambrook et al. *Molecular Cloning: A Laboratory Manual,* 2d ed. Vol. 1, pp. 1.101-104, Cold Spring Harbor Laboratory Press (1989) (hereby incorporated by reference), and include use of a prewashing solution of 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

In some embodiments, the binding agents hybridize to a target sequence in a sample under low stringent conditions. Low stringency conditions may include, as used herein, conditions that can be readily determined by those having ordinary skill in the art based on, for example, the length of the DNA. Low stringency may include, for example, pretreating the DNA for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ CPM binding agent is used. Samples are incubated in hybridization mixture for 18-20 hours at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C.

In other embodiments the invention may relate to binding agents that are peptide sequences or comprise peptide sequences that are derived from non-antibody proteins, e.g. peptide sequences derived from nucleic acid binding domains of different proteins, ligands of different cellular and nuclear receptors and their derivatives. Some non-limiting examples of such binding agents may be c1q protein of the classical pathway of the complement cascade which can bind to an antibody constant region, a MHC molecule, e.g., MHC class I and MHC class II and non conventional MHC, a molecule having a specific binding partner, such as molecules involved in cellular signaling pathways such as molecules having leucine zipper domains, e.g., fos/jun, myc, GCN4, molecules having SH1 or SH2 domains, such as Src or Grb-2; an immunoglobulin receptor, e.g., an Fc receptor; a chimeric protein, i.e., a protein engineered to combine the features of two or more specific binding partners, e.g., a leucine zipper could be engineered into a Fc region of an antibody, an SH2 domain could be engineered to be expressed in a Fc region of an antibody. In other embodiments, fusion proteins can be engineered comprising an Fc portion of an antibody with a substituted variable domain.

The binding agent may also be small molecules which can bind specifically to certain structural units of large biological molecules.

In some embodiments binding agents may comprises a detectable label, e.g. a fluorescent substance, hapten, enzyme, etc. In one embodiment, the invention relates to labeled binding agents, i.e. labeled third or further binding agents, that are capable of specifically binding to the deposited detectable molecules and are used for visualization of target sites of the invention. In one embodiment, the invention relates to a binding agent comprising an enzyme label. Non-limiting examples of suitable enzyme labels may be horseradish peroxidase (HRP), alkaline phosphatase (AP), beta-galactosidase (GAL), glucose-6-phosphate dehydrogenase, beta-N-acetylglucosaminidase, β-glucuronidase, invertase, xanthine oxidase, firefly luciferase, glucose oxidase (GO). In one embodiment a binding agent may comprise HRP as a label. In another embodiment, a binding agent may comprise AP as a label.

In some other embodiments, relatively small molecules of binding agents conjugated with an enzyme of the invention may be preferred, e.g. isolated Fab fragments of antibodies conjugated with one, or two, or more moieties of an enzyme, e.g. HRP. Such binding agents are relatively compact molecules and this may be advantageous for detecting individual units of targets that are "hidden" or masked in a target or in a sample by other molecules of the surroundings; single target structures of interest that may be hidden within the target molecule; single viral particles that may be hard to reach in complicated biological samples comprising cells. It may also be advantageous to use such binding agent in order to reduce unspecific binding of the agents to target unrelated objects in the sample. In one embodiment, use of small binding agent constructs, such as $(Fab)_1$-$(HRP)_1$, in particular, as the first binding agent, wherein the Fab fragment is derived from a polyclonal antibody, or a second binding agent, wherein the Fab fragment is derived from the secondary polyclonal antibody, may be advantageous for detection of targets present in samples at very low amounts (i.e. amounts that are undetectable by any other known in the art visualization method employing an enzyme-mediated deposition of stain). Use of such Fab binding agents allows multiple specific binding the binding agent to their binding partners in the sample and, at the same time, massive labeling of their binding partner with multiple enzyme labels. This allows to significantly enhancing reporter deposition at sites of the sample comprising the multiple enzyme labels.

In other embodiments, it may be advantageous use of large binding agent constructs, such as conjugate molecules comprising a core polymer that is chemically linked to multiple specific binding agents (e.g. antibodies) and, optionally, to one or multiple labels. Both latter constructs may increase the level of specific target staining and decrease unspecific staining. Further, large conjugates comprising a binding agent and tens to hundreds enzyme moieties may be advantageous e.g. in cases where a very fast target detection is concerned or obtaining large deposits per individual target site is desirable. These constructs may also be recommended when a target is present in the sample at very low amounts.

Amounts of binding agents necessary for forming target sited of the invention may vary depending on different factors, e.g. sample species, target species, binding agent species, binding affinity of binding agents, etc. Using common general knowledge the skilled in the art can select an appropriate binding agent and determine the amount needed for every particular embodiment. In some embodiments it may be preferred that the amounts of binding agents forming the target sites are adjusted so that not all single units of a target present in the sample, but a fractional sub-population thereof is involved in formation of target sites of the invention, e.g. in embodiments when the sample comprise a target in abundant amounts, or a target present in a broad dynamic concentration range. In other embodiments, it may be preferred that all or substantially all single units of a target are involved in formation of target sites of the invention, e.g. in case of samples with a very low target expression of a target or single units of a target. In the latter embodiments, it may be preferred to use binding agents in amounts that will secure formation of binding sites with a substantial majority of individual single units of the sample, i.e. a substantial majority of single units of a target present will be involved in formation the target sites.

Enzyme

According to the invention a target in a sample is visualized by depositing a detectable substrate of an enzyme with oxidoreductase activity at sites of the sample comprising immobilized target, wherein said sites comprise said enzyme.

The enzyme according to the invention is an enzyme with oxidoreductase activity (interchangeably termed herein as "oxidoreductase" or "enzyme of the invention").

By the term "enzyme with oxidoreductase activity" is meant an enzyme classified as EC 1 in the EC number classification of enzymes that catalyzes the transfer of electrons from one molecule (the reductant, also called the hydrogen or electron donor) to another (the oxidant, also called the oxygen or electron acceptor). In preferred embodiments, the invention relates to oxidoreductases classified as E 1.10. (phenoloxidases) and E 1.11. (peroxidases).

In one preferred embodiment the invention relates to phenoloxidases, in particular to the family of copper-containing oxidase enzymes, laccases (E 1.10.3.2). Laccases act on phenols and similar molecules, performing one-electron oxidation. Laccases play a role in the formation of lignin by promoting the oxidative coupling of lignols, a family of naturally occurring phenols. A laccase suitable for the purposes of the invention may be for example an enzyme described by Phillips L E and Leonard T J (Benzidine as a Substrate for Measuring Phenoloxidase Activity in Crude Cell-Free Extracts of *Schizophyllum commune*. Mycologia 1976, 68: 277-285), or Kunamneni A, Plou F J, Ballesteros A, Alcalde M. (Laccases and their applications: a patent review. Recent Pat Biotechnol. 2008, 2(1):10-24), or Rodriguez Couto S, Toca Herrera J L (Industrial and biotechnological applications of laccases: a review. Biotechnol Adv. 2006, 24(5):500-13.)

The term "laccase" is used herein to designate an enzyme with phenoloxidase activity of the invention, however it is understood then laccase is one of many embodiments of penoloxidase that are suitable for the purposes of the invention.

Laccase belongs to the oxidase enzyme family it requires oxygen as a second substrate for the enzymatic action. The source of oxigen for the deposition reaction of the invention when the enzyme is a laccase may be in one embodiment a peroxyde compound present in the deposition media, in another embodiment it may be the oxygen present in the air.

In another preferred embodiment, the invention relates to a peroxidase enzymatic activity catalyzing a reaction of the form:

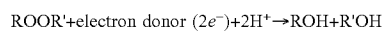

$$ROOR' + \text{electron donor } (2e^-) + 2H^+ \rightarrow ROH + R'OH$$

In one preferred embodiment of the invention, the enzyme with peroxidase activity is horseradish peroxidase (HRP). In another embodiment of the invention, the enzyme with peroxidase activity is soyabean peroxidase (SP).

The deposition media according to the invention, in embodiments when the oxidoreductase enzyme is a peroxidase, comprises a peroxide compound.

For some peroxidases the optimal substrate is hydrogen peroxide, some others are more active with organic hydroperoxides such as organic peroxides. The nature of the electron donor is very dependent on the structure of the enzyme, e.g. horseradish peroxidase (HRP) can use a variety of organic compounds both as electron donors and acceptors. HRP has an accessible active site, and many compounds can reach the site of the reaction.

The enzymatic activity, i.e. oxidoreductase activity, e.g. phenoloxidase or peroxidase activity, may be represented by a full-length molecule of an enzyme which is directly or indirectly linked to the molecule of a binding agent, or a fragment of the enzyme conflated with the enzymatic activity, e.g. 51% to 99.9% of the full size of the enzyme molecule, or less than 51%, e.g. 40%, 30% or less.

According to the invention, a binding agent may be directly or indirectly conjugated with one or more enzyme moieties, (the term "moiety" in the present content means a part of molecule of the enzyme that is capable of oxidoreductase activity, it includes both entire or substantially entire enzyme molecule and portions of said molecule of any size that are still capable of oxidoreductase enzymatic activity). Molecules of both or either first and/or second, third, etc. binging agents may be conjugated with one or several functionally active moieties of an oxidoreductase. In one embodiment at least one molecule of a first binding agent may be conjugated with one or more enzymatic moieties capable of oxidoreductase activity; in another embodiment at least one molecule of a second binding agent may be conjugated with one or more such moieties. The term "directly conjugated" means that an enzyme moiety is linked to a molecule of a binding agent via a chemical bond. The term "indirectly conjugated" means that a moiety of an enzyme is associated with the molecule of a binding agent via a linking molecule, which has a chemical bond with binding agent and a chemical bond with the enzyme. Methods of conjugating biological molecules and linker molecules are well-known in the art and exemplified below.

In one embodiment the moiety of oxidoreductase is a moiety of HRP, e.g. the whole HRP molecule a fragment thereof that is capable of the HRP enzymatic activity, it may also be a recombinant protein comprising the part of HRP that possesses the enzymatic activity, etc. In another embodiment the moiety of oxidoreductase may be a moiety of soybean peroxidase (SP). In another embodiment the moiety of oxidoreductase may be a moiety of laccase.

Non-limiting examples of binding agents which comprise an enzyme with oxidoreductase activity may be antibody molecules or derivatives thereof, e.g. Fab fragments conjugated with one or more moieties of HRP, and nucleic acid binding agents conjugated with HRP, etc. Such binding agents may bind directly or indirectly to single units of a target, e.g. a single target molecule, and form thereby complexes, wherein the single complex comprises a single individual unit of the target and one or more of binding agents wherein one or more of the binding agents comprise an enzyme with oxidoreductase activity.

In one embodiment the binding agent may be a conjugate comprising one, or two or more moieties of a peroxidase, or another enzyme of the invention, wherein said moieties are linked to the binding agent, e.g. an antibody molecule conjugated with one or more moieties of HRP. In another embodiment the binding agent may be a conjugate that comprises two or more enzymes with peroxidase activity, e.g. two or more moieties of HRP, that are linked to the binding agent indirectly, e.g. one or more molecules of an antibody and one or more HRP moieties independently linked to a backbone polymer.

The number of HRP per molecule of a binding agent may vary from 1 enzyme moiety per a binding agent to 20-50 per a binding agent or more. In some embodiments it may be preferred to use binding agents wherein the number of HRP moieties is at least two, preferably from two to twenty five enzyme moieties per binding agent, e.g. between three and twenty, such as 4, 5, 6, 7, 8, 9, 10 etc. Using binding agents, wherein the number of the enzyme moieties per binding agent is two or more may be preferred wherein a target is desired to visualized in the sample as a distinct dot (such as a dot of color, fluorescence or radioactivity). In some embodiments it may be preferred to use binding agents comprising more than four enzyme moieties per binding agent per binding agent, preferably between 5 and 20, for example from 5 to 15. Binding agents with more than four enzyme moieties are favorable for formation of target sites which can be visualized as visually distinct dots of substantially identical size. In some embodiments, it may be preferred that substantially all binding agent molecules associated with the enzyme comprise approximately the same number of enzyme moieties per molecule, e.g. 4-6, 5-7, 6-8, 7-9, 8-10, etc per binding agent molecule, e.g. 4-6 or 6-8 HRP moieties per an antibody molecule. A binding agent according to the invention may also comprise a combination of moieties of different oxidoreductase enzymes.

A single unit of a target inherently comprising an oxidoreductase activity or is bound (directly or indirectly) to a binding agent comprising an enzyme with oxidoreductase activity, e.g. peroxidase activity, constitutes a single target site of the invention. In one embodiment, a single target site of the invention may comprise a single target unit, at least one first binding agent and at least one second binding agent, wherein the at least one second binding agent is conjugated with one or more enzymes with peroxidase activity, e.g. HRP. In another embodiment, a single target site may comprise a single unit of a target, at least one first binding agent conjugated with a hapten and an anti-hapten antibody, wherein the anti-hapten antibody is conjugated with one, two or more enzymes with peroxidase activity, e.g. HRP. In another embodiment, the target site may comprise a single target unit and a first binding agent comprising an oxidoreductase activity, e.g. one or more moieties of HRP. Target sites of the invention may comprise any combination of a single unit of target (of any of the discussed above) with any binding agents discussed above, wherein said combination comprises an oxidoreductase activity, e.g. peroxidase activity, e.g. HRP.

A single target site of the invention in one embodiment may be a single site of a solid support (as any of the discussed above) comprising a single unit of a target comprising the enzymatic activity of the invention. As discussed above, in some embodiments, an oxidoreductase enzyme may in itself be the target, accordingly, an oxidoreductase enzyme, e.g. HRP, SP, laccase, etc, immobilized onto or within a solid support may be the target site of the invention.

Enzyme Substrates

To visualize a target inherently comprising or associated with an oxidoreductase activity, a sample comprising thereof is incubated in an aqueous solution comprising a first substrate of the enzyme associated with the target site of the invention, and a second substrate of the enzyme.

The first substrate of the enzyme associated with a target site of the invention according to the invention is alpha-cyano-4-hydroxycinnamic acid (ACHCA) (I)

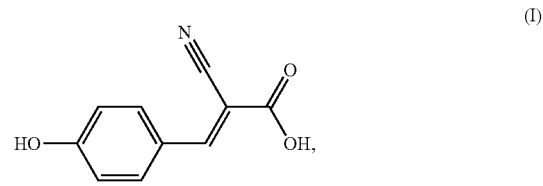 [SMILES: N#C/C(=C\c1ccc(O)cc1)C(=O)O]

(I)

or a derivative thereof.

The present invention utilizes the capacity of ACHCA to form a stable radical which can cross-link molecules of the second substrate (described below) in the presence of an enzyme with oxidoreductase activity, e.g. in the presence of horse radish peroxidase (HRP) at the target site and a peroxide compound in the deposition media, and deposit the cross-linked molecules of the second substrate at single target sites, i.e. in the vicinity on the target associated with the enzyme.

The invention also relate to derivatives of ACHCA, wherein the term "derivative" means a compound that is derived or derivable from ACHCA via substitution of one or more atoms of ACHCA for other atoms and has substantially all the features of ACHCA that are necessary to serve as the first substrate, in particular, a compound that under conditions of the invention (1) is a water soluble electron rich organic compound, (2) is capable of generating a radical upon a reaction with an enzyme associated with the target, and (3) is capable of cross-linking water soluble molecules of a second substrate of said enzyme producing thereby a water insoluble polymeric product of said second substrate.

To produce deposits of the second substrate under conditions of the invention amounts of ACHCA in the aqueous solution may vary from about 0.15 mM to about 30 mM or more, e.g from around 0.5 mM to around 1 mM, around 1.5 or around 1.75 mM, around 2 mM, around 2.5 mM, around 3 mM, between 3 mM and 4 mM, between 4 mM and 5 mM, between 5 mM and 6 mM, between 6 mM and 7 mM, between 7 and 8 mM, between 8 mM and 9 mM, between 9 and 10 mM, between 10 mM and 11 mM, between 11 mM and 12 mM, between 12 mM and 13 mM, between 13 mM and 14 mM, between 14 mM and 15 mM, from 15 mM to 20 mM, between 20 and 30 mM, between 30 and 50 mM (including both end points of all mentioned intervals and any value within). In one preferred embodiment, the amount of ACHCA may be in the range of from around 0.75 mM to around 5.75 mM. The term "around" in the present context means+/−0.05-0.5 mM. These amounts provide slower deposition of the second substrate and allow forming large deposits at single target sites, which may be visualized in the sample as dots of around 1 to around 3 microns in diameter. The term "around" in the present context means+/−0.05-0.5 microns. In another embodiment, the amount of ACHCA may be in the range from around 5.85 mM to around 30 mM or more, such as between 30 mM and 50 mM. These amounts of ACHCA promote speeding up the deposition reaction, i.e. the formation of deposits of the second substrate and do not allow forming very large deposits of the second substrate at single target sites. The deposits of the second substrate are visualized in this case as a homogeneous stain similar of a conventional histological stain obtained by using the HRP or AP-based visualization systems well-known in the art, however with significantly increased crispness of the staining.

Deposits of the second substrate may be directly detectable by visual means, such as microscopic optics, when the conjugate comprises a chomogenic, fluorescent or luminescent label. In other embodiments, e.g. when the conjugate comprise a member of a specific binding pair or a radioactive compound as detectable label, the precipitated second substrate may be detected in steps following the deposition. In both cases, the deposits of the second substrate will "report" to the observer the presence of target at the deposition site. So, the molecule of second substrate of the invention is interchangeably termed herein as "reporter".

The second substrate of an enzyme of the invention is a conjugate molecule comprising one or more compounds that are capable of serving as substrates of said enzyme and a detectable label, wherein the detectable label is selected from the group consisting of a fluorescent, luminescent, radioactive or chromogenic compounds or members of specific binding pairs.

A conjugate molecule as the second substrate of the invention has the following features:
1. It is water soluble;
2. It does not precipitate from an aqueous solution containing ACHCA (and containing a peroxide compound) in the absence in the environment of an enzyme with oxidoreductase activity (peroxidase);
3. It does not precipitate from an aqueous solution that does not contain ACHCA (but containing a peroxide compound) in the presence of an enzyme with oxidoreductase activity (peroxidase);
4. It precipitates from an aqueous solution containing ACHCA (and a peroxide compound) in the presence of oxidoreductase activity (peroxidase) in the environment.

Thus, the invention relates to the second substrate which is a water soluble conjugate molecule that can be described by the following formula (II):

$(Y)n\text{-}L\text{-}(Z)m,$ wherein
Y is a moiety capable of serving as substrate of an enzyme with oxidoreductase activity;
Z is a detectable label;
L is a linker compound or a bond,
wherein
n is an integer from 1 to 150, and
m is an integer from 1 to 150.

In some embodiments a water soluble conjugate molecule of the invention may additionally comprise moieties that may enhance its features, e.g. improve its capacity as the label or enzyme substrate, or increase/reduce its water solubility.

In one preferred embodiment Y is selected from compounds of the following formula (II):

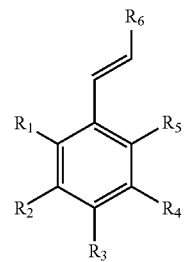

wherein
R1 is —H, —O—X, N(X)$_2$ or —S—X;
R2 is —H, —O—X, —N(X)$_2$, or —S—X,
R3 is —H, —OH, —NH$_2$ or —SH;
R4 is —H, —O—X, —N(X)$_2$, or —S—X,
R5 is —H, —O—X, N(X)$_2$, or —S—X,
R6 is —CON(X)$_2$, or CO—X,
wherein
H is hydrogen;
O is oxygen
S is sulphur
N is nitrogen, and
X is H, alkyl or aryl.

One preferred embodiment is that the conjugate comprises at least two compounds Y of the formula (ii).

In one embodiment at least two of the compounds Y are identical compounds of the formula (ii). In one embodiment at least two of the compounds Y are different compounds of the formula (ii).

Preferably a residue Y defined by the formula (ii) is connected to a linker L via group R6.

In one embodiment, at least one compound Y is a residue of ferulic acid, or a derivative thereof. Non-limiting examples of other compounds that are suitable as the Y-compounds of the invention are described in EXAMPLES.

In one preferred embodiment, the conjugate comprises two to four compounds Y. In one preferred embodiment, a conjugate may comprise 2 to 4 residues of ferulic acid or residues of derivatives thereof, for example 2, 3 or 4 residues. In one embodiment, all compounds Y of the conjugate are residues of ferulic acid.

In some embodiments the number of Y compounds may be higher than 4, e.g. such as 5-10, 10-15, 15-20, 20-50, 50-100, or 100-150 compounds.

According to the invention, Y compounds are located in a conjugate molecule as a group, preferably grouped as two to four Y compounds per group, (i.e. a conjugate comprising more than four Y compounds may comprise several groups of two to four Y compounds, wherein said groups are separated in the conjugate molecule by a group of atoms, e.g. by a molecular distance corresponding to 5 to 30 interconnected atoms or more). Preferably, the two to four Y compounds in such groups are linked together via a spacer compound that makes a distance between two neighboring Y residues which is not longer than 5-15 interconnected atoms, e.g. 5-10, 6-12, 7-13, 8-14, 9-15, etc., For example, 2-4 Y compounds may be attached to amino acids making up a peptide chain comprising 2 to 4 amino acid residues, e.g. residues of lysine, serine, cystein, etc., wherein the Y compounds are attached to reactive groups of the amino acid residues of the peptide, e.g. to the epsilon amino groups of lysine residues. Two to four compounds Y may also be connected to each other via other short polymers which comprise a number of brunching points, wherein a molecular distance between these branching points corresponds to a chain of not more than 3-7 atoms, preferably 3-5 atoms, wherein the Y compounds may be directly indirectly linked to said branching points. Two to four compounds Y may also be grouped together being conjugated to a non-polimeric molecule that have two to four reactive groups allowing attaching any two to four Y compounds. Such grouped location of Y compound is termed thereafter "Y-head" of the conjugate molecule.

Close spacing of multiple (at least two) Y compounds in conjugate molecules has the effect that the conjugates remain soluble in aqueous solutions containing a peroxide compound and ACHCA at the absence an enzyme with oxidoreductase activity in the environment and precipitate very quickly from such solutions when the solutions are contacted with the enzyme. This is in contrary to conjugates that comprise a single Y compound or comprise several Y compounds that are not concentrated in the conjugate molecule to form an Y-head, Such compounds precipitate slower and may be not efficient enough to provide massive and crisp deposits at the target sites (visualized as a crisp homogeneous stain or distinct dots (of color, fluorescence, or radioactivity) having an approximate diameter of 2-3 microns).

In one preferred embodiment, the Y-head comprises two to four Y-residues linked together via a short polymer, e.g. a short PNA molecule or a short peptide, wherein the peptide, preferably, comprises lysine, serine glutamate and/or cystein residues. However, any other polymeric or non-polymeric water soluble molecules that comprise 15 or less atoms that can be conjugated with at least two Y-residues and a linker L may be suitable.

The detectable label of a conjugate molecule may be any substance which can be visually detected, e.g. a fluorescent or luminescent substance, or any substance that can be detected by using some detecting means, e.g. a radioactive label, a member of a specific binding pair, e.g. a nucleic acid sequence, hapten, etc.

Any fluorescent, luminescent, bioluminescent or radioactive molecules may be used as the labels. Many of them are commercially available, for example fluorescent stains Alexa Fluors (Molecular Probes) and DyLight Fluors (Thermo Fisher Scientific). Other non-limited examples of fluorescent labels may be the following molecules: 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, Cy2, Cy3, Cy5, AMCA, PerCP, R-phycoerythrin (RPE) allophycoerythrin (APC), Texas Red, Princeton Red, Green fluorescent protein (GFP) coated CdSe nanocrystallites, ruthenium derivatives, luminol, isoluminol, acridinium esters, 1,2-dioxetanes and pyridopyridazines, radioactive isotopes of hydrogen, carbon, sulfur, iodide, cobalt, selenium, tritium, or phosphor. Some nonlimiting example of stain labels are described in Examples.

In some embodiments the detectable label may be an enzyme. Non-limiting examples of suitable enzyme labels may be alkaline phosphatase (AP), beta-galactosidase (GAL), glucose-6-phosphate dehydrogenase, beta-N-acetyl-glucosaminidase, β-glucuronidase, invertase, xanthine oxidase, firefly luciferase, glucose oxidase (GO).

In other embodiments, the detectable label may be a member of a specific binding pair, e.g. a hapten. As non-limiting examples of suitable haptens may be mentioned 2,4-dinitrophenol (DNP), digoxiginin, fluorescein, Texas Red, tetra methyl rhodamine, nitrotyrosine, acetylamino-flurene, mercury trintrophonol, estradiol, bromodeoxy uridine, dimethylaminonaphthalene sulfonate (dansyl), amino acids tyrosine, serine, etc. As examples of suitable specific binding pairs may also be mentioned biotin, streptavidin, complementary natural and non-natural oligonucleotide sequences, zink fingers binding domain pairs, etc. Other examples are discussed above.

In one preferred embodiment the label may be a member of a specific binding pair, e.g. a hapten. In another preferred embodiment, the label may be a fluorescent substance. In another preferred embodiment, the label may be a chromogen. Other labels may be preferred in other embodiments.

As mentioned, the number or detectable labels per conjugate molecule (as any of the described above) may vary. In some embodiments the number of labels may be from 1 to 3, for example 1, 2 or 3 labels per conjugate molecules. In some other embodiments, the conjugate may comprise more from 4 to 150 labels per conjugate molecule. In some preferred embodiments, conjugate molecules may comprise one detectable label.

In some embodiments, when the conjugate comprises more than 1 label, it may be preferred that the labels are grouped so that there is a certain molecular distance between the labels, e.g. such as a chain of 10-15 atoms or more, e.g. up to 30, 60 or 90 atoms (such arrangement of labels is in the conjugate molecule is termed herein Z-tail). It is preferred that a linker compound separating the labels is hydrophilic.

In one embodiment multiple labels of a conjugate molecule of the invention may be identical detectable substances, in another embodiment the labels may be different detectable substances.

In one preferred embodiment a conjugate molecule may comprise one Y-head (as any of the discussed above) and one label, however, in other embodiments conjugate molecules that have a different composition of Y and Z compounds may be preferred.

In a conjugate molecule a detectable substance (a single label or a plurality thereof) may be separated from Y compounds by some molecular distance. This molecular distance corresponds to a compound that links the Y compounds and Z label(s) in the conjugate.

The linker compound may be a small molecule, such as e.g. a single amino acid, or it may be a relatively large molecule, such as a chain comprising up to 150 atoms or more. In any case, the linker compound of the conjugate is a water soluble molecule that comprises at least two branching points which are distanced from each other in the molecule by at least 2 interconnected atoms. By the term "branching point" is meant a point in a molecule wherein other molecules may be attached. The branching point may be an atom, a group of atoms, or a functional group via which compounds Y and Z may be linked to the molecule. It was surprisingly found that a linker comprising from 4 to 150 atoms which separate the labels Z and enzyme substrates Y provides most efficient deposition of the conjugates under conditions of the invention. Other advantages of such arrangement of Y and Z compounds to mention are: (1) conjugates comprising multiple hydrophobic labels remain good solubility in water solutions, and (2) the labels are better accessible for binding agents, when binding agents are used to detect the deposited conjugates.

In one embodiment, L may be a bond, such as a covalent bond between an atom of a label Z and an atom of a compound Y. The invention also relates to L as bond, when there is no linking compound between an Y compound or Y-head and a label Z or Z-tail, i.e. an Y or Y-head comprising two to four compounds Y is directly or indirectly, e.g. via a lysine residue, linked by a bond (L) to a label Z or Z-tail. Such reporters may be advantageous when it is desired to visualize a target as smaller dots (i.e. dots of a diameter less than 3 microns, e.g. around 1-1.5 microns).

In one preferred embodiment one Y-head comprising two to four compounds Y may be directly or indirectly, e.g. via lysine residue (Lys), linked to a linker compound (L), which a polymer comprising two or five repeats of the following formula

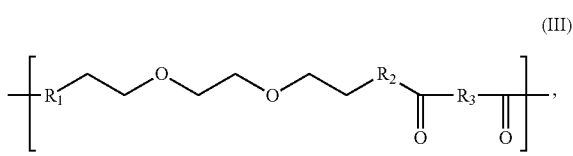

(III)

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups. Depending on the number of repeats of the formula (III) (2 to 5) the L molecules of this formula are termed L30 (2 repeats), L60 (4 repeats), etc. Their synthesis is in detail described in WO2007/015168. The resulting conjugate, i.e. $(Y)_{2-4}$-(Lys)-L-, may be further (directly or indirectly, e.g. via lysine residue) conjugated with one (or more) detectable label making a molecule such one of the formula $(Y)_{2-4}$-(Lys)-L-(Lys)-(Z)$_{1(or\ more)}$, or it may be conjugated with another water soluble molecule, such as e.g. a dextran polymer (Dex), which comprises one or more reactive groups allowing attaching one or several such conjugates, making a molecule such as one of the formula $((Y)_{2-4}$-(Lys)-(L))$_n$-Dex-(Lys)-(Z)$_1$-((Lys)-L-Z)$_m$, wherein m and n are integers from 1 to 150 or more. Synthesis of such conjugates is described in EXAMPLES.

In other preferred embodiments, Y compounds may be connected to Z labels through a linker compound that is a small molecule, such as e.g. an amino acid, e.g. lysine, beta-alanine, glycine, or other small water soluble molecules that have at least two branching points. By the term "branching point" is meant a point in a molecule wherein other molecules may be attached. The branching point may be an atom, a group of atoms, or a functional group via which compounds Y and Z may be linked to the molecule.

There is a great variety of molecules that may be used as linker L. Examples of polymer molecules suitable as linker of the invention include, but not limited to, polysaccharides such as dextrans, carboxy methyl dextran, dextran polyaldehyde, carboxymethyl dextran lactone, and cyclodextrins; pullulans, schizophyllan, scleroglucan, xanthan, gellan, O-ethylamino guaran, chitins and chitosans such as 6-O-carboxymethyl chitin and N-carboxymethyl chitosan; derivatized cellolosics such as carboxymethyl cellulose, carboxymethyl hydroxyethyl cellulose, hydroxyethyl cellulose, 6-amino-6-deoxy cellulose and O-ethylamine cellulose; hydroxylated starch, hydroxypropyl starch, hydroxyethyl starch, carrageenans, alginates, and agarose; synthetic polysaccharides such as ficoll and carboxymethylated ficoll; vinyl polymers including poly(acrylic acid), poly(acryl amides), poly(acrylic esters), poly(2-hydroxy ethyl methacrylate), poly(methyl methacrylate), poly(maleic acid), poly(maleic anhydride), poly(acrylamide), poly(ethyl-co-vinyl acetate), poly(methacrylic acid), poly(vinylalcohol), poly(vinyl alcohol-co-vinyl chloroacetate), aminated poly (vinyl alcohol), and co block polymers thereof; poly ethylene glycol (PEG) or polypropylene glycol or poly(ethylene oxide-co-propylene oxides) containing polymer backbones including linear, comb-shaped or hyperbranched polymers and dendrimers, including branched PAMAM-dendrimers; poly amino acids including polylysines, polyglutamic acid, polyurethanes, poly(ethylene imines), pluriol; proteins including albumins, immunoglobulins, and virus-like proteins (VLP), and polynucleotides, DNA, PNA, LNA, oligonucleotides and oligonucleotide dendrimer constructs; mixed polymers, i.e., polymers comprised of one or more of the preceding examples of polymers, co-block polymers and random co-polymers.

Properties of the chosen polymer can be modified to optimize performance, e.g. the length or branching can be optimized. Furthermore, the polymer may be chemically modified to carry various substituents. The substituents may be further chemically protected and/or activated, allowing the polymer to be derivatized further.

In one preferred embodiment the linker compound between oxidoreductase substrates and labels is a dextran polymer or a conjugate molecule comprising a dextran polymer.

Methods of conjugating polymers with different chemical substances, e.g. labels, are well known in the art and can be used to make conjugates of the invention. For example, the polymer may be activated with vinylsulfon and mixed with a detectable label and a molecule of formula (II) to form the polymer conjugate. In other embodiments, aldehydes can used to activate a polymer, e.g. dextran, which is then mixed with a detectable label and a molecule of formula (II). Yet another method of preparing polymeric conjugates is by using so called chemo selective coupling schemes for coupling the components together, e.g. molecules can be derivatized with thiol reactive maleimide groups before being covalent coupled to an thiol modified polymeric backbone. In some other embodiments, a molecule for formula (I) and a detectable label can be attached to the polymer via a linking compound. Examples of this method include the use of homobifunctional linker compounds such as glutaric dialdehyde, hexan di isocyanate, dimethylapimidate, 1,5-difluoro-2,4-dinitrobenzene, heterobifunctional cross binders like e.g. N-gamma-maleimidobytyroloxy succinimide ester, and zero length cross binders such as 1-ethyl-3-(3-dimethylaminopropyl)cabodiimide.

Methods of derivatization of polymers comprising one or more repeats of formula (III) (termed hereafter "L30") are described in detail in WO2007/015168. Exemplary conjugates comprising linkers that are polymers comprising various number of repeats of formula (III), such as a polymer comprising two L30 repeats, (termed L60), such as a polymer comprising three L30 repeats (termed L90), such as a polymer comprising five L30 repeats (termed L150) are described in EXAMPLES.

Non-limiting examples of small L compounds may be different single amino acid residues, short peptide sequences, or the like.

Conjugate molecules comprising one or more compounds Y (in particular, wherein the Y compound is defined by the formula (ii) above), one or more labels Z (as any of the discussed above) and linkers L, in particular, conjugate molecules, wherein the linker L is a bond (e.g. a covalent bond) or small compound, are an independent aspect of the invention. Generally, the invention relates to conjugates that comprise one or more compounds Y of the formula (ii). In one embodiment, the invention may relate to conjugates comprising a single Y of the above formula, wherein all four R1, R2, R4 and R5 are not simultaneously —H and R3 is not —OH, but, still, in another embodiment, it may relate to conjugates comprising at least two such Y compounds.

The amount of the second substrate in the aqueous solution may vary from about $10^{-10}$ M to about $10^{-4}$ M depending on the physical nature of the detectable label, for example, in case the conjugate (as any of the described above) comprises a radioactive label, the amount of said conjugate in the aqueous solution may be in the range from about $10^{-10}$ M to about $10^{-6}$ M, and in the range from about $10^{-9}$ M to about $10^{-4}$ M, in case the conjugate comprises a fluorescent label or a label which is a member of a specific binding pair.

Non-limiting examples of conjugate molecules are described in EXAMPLES.

Incubation Media

According to the invention, to visualize a target comprising enzymatic activity of the invention (in particular, peroxidase activity), a sample supposedly comprising the target is incubated in an aqueous solution comprising compounds of the visualization system described above (i.e. the first substrate and second substrate, optionally, a peroxide). In some embodiments, the sample may be subjected to several incubations in other aqueous solutions, e.g. in an aqueous solution comprising one or more binding agent, etc. These aqueous solutions are generally termed herein as "incubation media", wherein the term "incubation media" means an aqueous solution where the sample is maintained during a certain period of time (termed herein "incubation time") in order to accomplish a desirable reaction.

Time for maintaining/incubating of the sample in an incubation media, i.e. incubating time, may vary depending on the technical effect which is desired to be achieved during the incubation. In different embodiments an incubation may lasts from approximately 3 seconds to approximately 3 min, e.g. around 10 seconds, 20 seconds, 30 seconds, 1 minute, 2 minutes, 5 minutes, 10 minutes. or longer, e.g. one-two hours, overnight. In one embodiment, incubating time at all steps of the method may have the same duration, i.e. every incubating may lasts 5 to 10 minutes, etc. In one embodiment a sample in an aqueous solution comprising a binding agent (termed hereafter "binding agent solution") may be maintained during 1-3 minutes or shorter/longer, incubating in an aqueous solution comprising the components of amplification system of the invention (termed hereafter "deposition media") may lasts from around 30 seconds to around 10 minutes.

The incubating may be performed at various temperatures, depending on the type of target, binding agent, etc. The procedures according to the invention are basically not dependent on temperature and can be performed at a temperature from around +4 C.° to around +40 C.°, however, if desired, the temperature may be adjusted to speed up or slow down the reactions taking place during an incubation, e.g. it may be recommended to use lower temperatures to prolong the incubating time, and, vice versa, higher temperatures may be used to shorten the time for incubating.

Binding Agent Media

In one embodiment of the invention, the sample comprising a target may be incubated with one or more binding agents (as any of the described above). Accordingly, in one embodiment, the invention relates to an aqueous solution comprising a binding agent, e.g. a target specific binding agent or binding agent comprising an enzyme with oxidoreductase activity.

Incubation of a sample comprising a target that does not have inherent oxidoreductase activity in such media allows forming target sites of the invention. Accordingly, the binding agent medium is an aqueous medium, in which the chosen binding agents are soluble and have their specific binding affinity to their binding partners in the sample. Basically, the binding agent medium is a buffered aqueous solution of one or more binding agents that has pH in the range from 4 to 9.

In some embodiments the binding agent medium may comprise an organic or inorganic salt. The inorganic salt may be selected form e.g. sodium chloride, magnesium chloride, potassium chloride, calcium chloride, sodium phosphate, or ammonium sulfate. The organic salt may be selected from e.g. sodium acetate, ammonium acetate or imidazole salts, e.g. imidazole hydrochloride, etc.

The amount of salt in a binding agent media may range from approximately $10^{-3}$ M to saturation, e.g. from approximately 20 mM to approximately 200 mM, or from approximately 50 mM to approximately 500 mM. In one preferred embodiment, the media may comprise salt in the amount from approximately 10 mM to 500 mM. In another preferred embodiment the medium may be free of salt.

As mentioned, typically, the pH value of a binding agent media may vary from about 4 to about 9, such as between pH 3.5 and pH 9.5, e.g. between pH 5 and pH 7, between pH 5.5 and pH 6.5 or between pH 6.5 and 7.5, or between pH 7 and pH 8, or between pH 7.5 and pH 8.5, or pH 8 and pH 9. Any buffer with a suitable buffer capacity may be used, e.g. phosphate buffered saline (PBS) and imidazole buffer. Other suitable buffer recommendations may be found in Good, N E., et al (1966) Hydrogen ion buffers for biological research. Biochem. 5(2), 467-477. The pH value of the media may be essential for binding of binding agent to the target; it may be optimized depending on the nature of the binding agent and the target.

In some embodiments the binding agent medium may comprise an organic modifier (by the term "organic modifier" is meant any non-aqueous solvent), e.g. N-Methyl pyrolidone (NMP), dimethylsulphoxide (DMSO), mono- and diethylene glycol, sulpholane, N,N-dimethylformamide (DMF), polyethylene glycol (PEG), propylene glycol, etc. The amount of the organic modifier may vary from around 1% to around 20% (v/v or w/v), or, in some embodiments, be higher than 20%.

In some embodiments the binding agent medium may comprise a detergent, e.g. polyethylenglycol-p-isooctyphenyl ether (NP-40)) or a surfactant (e.g. selected from the surfactants based on polyoxyethylene sorbitanmonolaurate (Tween), or a surfactant based on block copolymers (pluronic etc.), etc. The amount of the detergent may vary from about 0.001% to about 5%/v/v or w/v).

In some embodiments the binding agent medium may comprise a binding agent stabilizing agent, e.g. bovine serum albumin or dextran. The amount of the stabilizing agent may vary from 0.01% to 20% (w/v).

In some embodiments the binding agent medium may comprise an ion chelator (e.g. ethylene diamine tetra acetic acid (EDTA) or ethylene diamine hydroxyl phenylacetic acid type chelator (EDHPA), etc.). The amount of the chelator may vary from about $10^{-9}$ M to about $10^{-6}$ M.

In some embodiments, the binding agent medium may comprise one or more blocking agents for saturating non-specific binding sites, i.e. sites of the solid support that do not comprise the target. Some non-limiting examples of blocking agents suitable for different embodiments may be the Denhard's solution, bovine serum albumin, skimmed milk, etc.

As discussed above, the invention contemplates a great variety of species of targets, binding agents and assay formats, accordingly, composition of the binding agent medium may vary and may be adjusted for every particular embodiment using general knowledge of the art. Some non-limited examples of the binding agent medium are described in EXAMPLES.

The amounts of specific binding agents in the media may vary. These amounts are to be adjusted for every embodiment individually, depending on the nature and quality of binding agent(s), target, sample, reagents, assay format, etc. It may generally be recommended to use conditions of incubation and/or amounts of the binding agents in the incubation media that minimize unspecific binding of a binding agent in the sample. However, compared to many systems existing in the art, the power of signal amplification and flexibility of signal detection makes the described herein signal amplification system much less dependent on optimization of the binding agent media composition and incubation conditions. Generally, the amount of the first and/or second binding agent in a binding agent media may be recommended to be low, such as around or below the value of its Kd, e.g. range of 1-500 pM, however, higher amounts, i.e. higher than the binding agent Kd value, may also be used. A low amount of a binding agent having a high affinity to its binding partner combined with short incubation times, such as for example 0.5-10 minutes, allows specifically detect the target and reduce an unspecific binding. Signal amplification according to the invention is strong enough to visualize a target present in the sample in the broadest dynamic range, such as from a few single molecules of the target to a abundant amounts.

In some embodiments, a sample may comprise a target that is expressed abundantly or in a broad dynamic concentration range and it may be desirable to visualize single target units. Such the sample may be incubated in a binding agent media under conditions wherein the binding agents are capable of forming discrete single target sites only with a fractional subpopulation population of single target units. These conditions may include decreasing the amount one or more binding agents in the incubation media or, changing the composition of the binding agent medium such as pH, salt content, etc., or incubating conditions, such as temperature etc, may be adjusted so that they affect binding capability of one or more binding agents involved in formation of single target sites and the binding agents will therefore form the target sites only with a fractional subpopulation of single units of the target present in the sample. The term "fractional subpopulation" in the present context is defined a portion of the total population that is equal or less than 99%. e.g. equal or less than 90% of the total quantity of single units of the target in the sample, such as less than 85%, e.g. 75-80% of the total quantity of units of the target in the sample, such as less than 75%, for example from 1% to 50% of the total quantity of single units of the target in the sample, such as from 1% to 25% of the total quantity of units of the target in the sample, etc. In one embodiment, incubation conditions may be adjusted so that the binding agents will form discrete single target sites with a fractional subpopulation of single target units that is less than 1% of the total quantity of single units of the target present in the sample, such as from about 0.1% to about 1%.

In one embodiment, the binding agent media may comprise a binding agent which amounts are below the value of its dissociation constant (Kd) (or association constant (Ka) in case of antibody-antibody binding) relating to its binding to the affinity partner in the sample. In one embodiment, a first binding agent may be used in the amounts that are below its Kd relating to binding of said first agent to its target in the sample. In another embodiment, a second binding agent may be present in the amounts that are below its Kd relating to its binding to the corresponding partner in the sample. Use of very low amounts of binding agents that have an affinity partner in the sample, wherein said affinity partner is associated with the target site of the invention, is advantageous for reducing unspecific binding of the binding agents to objects that are unrelated to the target in the sample.

Deposition Media

To visualize a target, a sample supposedly comprising target sites of the invention is incubated in an aqueous solution comprising a first substrate of the enzyme with oxidoreductase activity and, a second substrate of the enzyme with oxidoreductase activity and, optionally, a peroxide compound (this media is termed herein "deposition media").

The deposition media may be an aqueous buffered solution with a suitable buffer capacity, e.g. phosphate buffered saline (PBS) and imidazole buffer. Other suitable buffers may be found in Good, N E., et al (1966) Hydrogen ion buffers for biological research. Biochem. 5(2), 467-477. The pH value of the solutions may be adjusted in order to achieve the technical effect of the incubation, namely formation of discrete deposits of the second substrate of an enzyme with oxidoreductase activity at discrete single target sites of the invention, for example adjusted to pH ranging from about 4 to about 9. However, pH of the aqueous solutions (i) and (ii) is of minor importance for the technical effect of the incubation.

The media may further comprise an organic or inorganic salt.

The inorganic salt may be selected form e.g. sodium chloride, magnesium chloride, potassium chloride, calcium chloride, sodium phosphate, or ammonium sulfate, etc.

The organic salt may be selected form e.g. sodium acetate, ammonium acetate or imidazole salts, e.g. imidazole hydrochloride, etc.

The amount of salt in the media may range from approximately $10^{-3}$ M to saturation, e.g. from approximately 20 mM to approximately 200 mM, or from approximately 50 mM to approximately 500 mM. In one preferred embodiment, the media may comprise salt in the amount from approximately 10 mM to 500 mM. In another preferred embodiment the medium may be free of salt.

The media may in different embodiments further comprise:
(i) an organic modifier and/or
(ii) an enzyme enhancer, and/or
(iii) an iron chelator, and/or
(iv) a detergent, and/or
(v) an anti-microbial agent The organic modifier may be present in the media in the amount from around 1% to around 20% (v/v or w/v), however, in some embodiments higher concentrations of the organic modifier may be required. The organic modifier may for example be polyethylene glycol (PEG). Other examples include but not limited to organic modifiers selected from the group essentially consisting of C1-C4, i.e. lower, alcohols, N-Methyl pyrolidone (NMP), dimethylsulphoxide (DMSO), mono- and diethylene glycol, sulpholane, N,N-dimethylformamide (DMF). In some embodiments it may be advantageous to use polyethylene glycol (PEG), e.g. PEG2000, or propylene glycol. The amount of polyethylene glycol in the media in these cases may vary from about 0.1% (v/v) to about 20% (v/v), for example from about 1% (v/v) to about 15%, such as 5-10% (v/v).

By the term "enzyme enhancer" is meant any compound which enhances the catalytic activity of peroxidase. Such enzyme enhancer may be selected from the group essentially consisting of phenylboronic acid derivatives and divalent metal ions such as nickel or calcium. The amount of the enzyme enhancer may vary from about $10^{-7}$ to about $10^{-3}$ M.

The iron chelator may be ethylene diamine tetra acetic acid (EDTA) or ethylene diamine hydroxyl phenylacetic acid type chelator (EDHPA). Concentration of the iron chelator may vary from about $10^{-9}$ to about $10^{-6}$ M.

The detergent may be selected from polyethylenglycol-p-isooctyphenyl ether (NP-40), a surfactant selected from the surfactants based on polyoxyethylene sorbitanmonolaurate (Tween), or a surfactant based on block copolymers (pluronic etc.). Concentration of the detergent may vary from about 0.001% to about 5%.

Embodiments of the first substrate and the second substrates are discussed in detail above.

The amount of the first substrate, i.e. ACHCA, in the media may vary. In some embodiments, it may be recommended to use ACHCA above 5.75 mM, such as from around 6 mM to around 15 mM, or higher. These amounts provide a crisp conventional target staining (i.e. as homogeneous stain). In other embodiments, it may be recommended to use ACHCA between around 0.15 mM and around 5.75 mM, such as from around 1 mM to around 5.5. mM. Such amounts of ACHCA provides staining of targets as distinct dots (of colour or fluorescence or the like) (see also discussion above).

The deposition media may comprise various amounts of the second substrate, such as from about $10^{-10}$ M to about $10^{-4}$ M, depending on the structure and composition of the conjugate, in particular the label it comprises. For example, in embodiments when the conjugate comprises a radioactive label, an applicable amount may be in the range from about $10^{-10}$ M to about $10^{-6}$ M. In other embodiments, e.g. when the conjugate comprises a fluorescent label or a label which is a member of a specific binding pair, the amount may be in the range from about $10^{-9}$ M to about $10^{-4}$ M. Some non-limiting embodiments are described in the EXAMPLES.

In one embodiment, the media may comprise a population of identical molecules of the second substrate. In another embodiment, the media may comprise a population of different molecules of the second substrate.

In some embodiment, in particular when the oxidoreductase enzyme is a peroxidase, e.g. HRP or SP, the deposition media preferably contains an amount of a peroxide compound. A preferred peroxide compound of the invention is hydrogen peroxide, however, other peroxide compounds may also be used in different embodiment, e.g. in some embodiments it may be preferred an organic peroxide such as e.g. tert-butyl peroxide, ditert-butyl peroxide, peracetic acid, etc, or in some embodiments it may be an adduct of hydrogen peroxide, such as hydrogen peroxide urea adduct.

The amount of a peroxide compound in the deposition media is preferably less than 5 mM, preferably in the range between 0.15 mM and 3.5 mM, e.g. in the range from around 0.25 mM to around 2.5 mM, between around 0.35 mM and around 1.5 mM, from around 0.5 mM to around 1 mM. The term "around" in the present context means +/−0.05-0.25 mM.

According to the invention a deposition media comprising the first and the second substrates of the enzyme is a stable solution, i.e. no precipitation of the enzyme substrates occurs and reactive capacity of the compounds with the enzyme is not affected for relatively long periods of times, such as up to 5 months storage at room temperature. The shelf-life of such media may be further prolonged when it stored at temperatures below +20° C., e.g. at +4-+10° C., and, optionally, an anti-microbial compound is added. The anti-microbial compound may be any anti-microbial compound commonly used for such purpose, e.g. sodium azid, Proclin™ or Bronidox®. Such stability of the solution has a particular advantage when automated procedures of visualization of targets are concerned.

Accordingly, one aspect of the invention relates to an aqueous solution comprising ACHCA and a conjugate molecule of the invention (as any of the defined above). The solution may be formulated as a concentrated deposition media (e.g. 2×, 3×, 4×, 5× to 10×, 10× to 20× concentrated or more) and diluted with water before mixing with a peroxide compound.

An aqueous solution comprising ACHCA and one or more conjugate molecules of the invention may be a part of a kit-of-parts for visualization of a target inherently comprising or linked to an oxidoreductase enzymatic activity in a sample in vitro. Such kit-of-part may further comprise a number of different compounds typically used for the target detection, e.g. binding agents, compounds relating to other visualization systems, etc. Accordingly, in one embodiment the invention relates to a kit-of-parts for an oxidoreductase-mediated visualization of a target in a sample.

Detection Media

In one embodiment the invention relates to a target visualization method which comprises one or more steps following the reporter deposition step, where the deposited reporter in detected. These steps comprise detection of on label associated with the deposited conjugate molecules at target sites. Accordingly, a sample comprising deposits of the reporter may be incubated in incubation media comprising a binding agent capable of specifically binding to a detectable label of the deposited conjugate molecules. Non-limiting embodiments of labels of the conjugate molecules and binding agents are described above and illustrated in EXAMPLES.

An incubation medium comprising a binding agent capable of specifically binding to a detectable label of the deposited conjugate molecules will typically have a similar or the same composition as the binding agent medium discussed above.

The binding agent bound to a detectable label of the deposited reporter may in one embodiment comprise an enzyme, e.g. horse radish peroxidase (HRP) or alkaline phosphotase (AP). Such binding agent can be detected using a standard visualization system employing chromogenic substrates of the enzymes, e.g. an enzyme substrate solution or a color developing solution. This kind of media may be any suitable media known in the art which is to be selected depending on available means for visualization and following the common general knowledge of the art concerning the nature of the detectable label of the deposits. Non-limiting examples of such detection are described in EXAMPLES.

Alternatively, in case the binding agent comprises HRP, a further step of incubation of a sample comprising the deposits of second substrate in the deposition media may be performed. Such further step may be advantageous in some embodiments when a signal associated with the deposited second substrate may weak, or the size of the primary deposit is relatively small, or it is desirable to change a signal associated with a deposit, e.g. from green to red color.

Additional deposition steps allows further amplifying of the signal associated with the deposit by increasing the amount of the deposited second substrate at target sites in further rounds of deposition according to the invention. Further deposition steps also allows modifying the character of the detectable signal, e.g. changing spectral characteristics of the signal, e.g. the initial label detectable as a red signal may be substituted for a label detectable as a green signal by using reporters comprising said green label for this additional deposition instead of reporters comprising a red label used in the initial deposition). Flexibility of the target visualization system of the invention do not add complexity to procedures or reagents used in additional steps of target detection, as all embodiments that relevant to incubation or deposition steps of the initial detection of the target (discussed above) may be used without substantial modifications in these addition steps.

In one embodiment the invention relates to washing media, i.e. media for removing the rests of compounds of the incubation medium from the sample after the incubation has been completed. The method of the invention may comprise one or more washing steps typically following a step of incubation of the sample in any media described above. Typically, a washing medium may be a buffered saline solution, water or an incubation media without reactive compounds, i.e. without binding agents, enzyme substrates and the like.

In one embodiment, the invention relates to a media for quenching the endogenous oxidoreductase activity. This type of media may be any media of such kind that is routinely used for the purpose in the art, for example a solution of hydrogen peroxide.

METHODS OF THE INVENTION

The following are non-limited embodiments of methods of the invention.

In one embodiment, the invention provides a method for visualization a target (as single target unities or the bulk), in samples, such as histological samples, wherein the target is immobilized, wherein said method comprises the following steps:

a) incubating a sample supposedly comprising one or more units of the target with one or more binding agents, wherein at least one of the binding agents is capable of directly binding to a unit of said target and wherein at least one of the binding agents comprises an enzyme with oxidoreductase activity, thereby forming one or more target sites, wherein a target site comprises a unit of the target and one or more binding agents, wherein at least one of the binding agents comprises the enzyme with peroxidase activity;

b) incubating sample (a) in an aqueous solution comprising
   i) a first substrate of said enzyme;
   ii) a second substrate of said enzyme, and, optionally,
   iii) a peroxide compound,
wherein the first substrate is alpha-cyano-4-hydroxycinnamic acid (ACHCA) or a derivative thereof and the second substrate is a conjugate molecule comprising at one or more compounds that is capable of serving as substrate of the enzyme with peroxidase activity and at least one detectable label;

c) detecting the label of the deposited discrete deposits at target sites.

The target sites may be visualized either as distinct dots (of color, fluorescence, luminescence or radioactivity) of about 2-3 microns in diameter, or a homogeneous stain without resolution into distinct dots using incubation conditions discussed above.

Depending on the nature of the label, the step (c) may comprise one or more further detection steps including different incubations with the label-specific binding agents and visualization agents. Some non-limiting embodiments of the latter are discussed above and illustrated in EXAMPLES.

Embodiments of binding agents, conjugate molecules, incubation media, visualizing means, etc. are discussed above.

In one preferred embodiment, the enzyme with oxidoreductase activity is a peroxidase, e.f. HRP or SP, and the deposition solution comprises a peroxide compound, e.g. $H_2O_2$.

In one embodiment the method above may comprise any further steps discussed above. In one embodiment, the method may comprise one or more steps following any of the steps a, b or c. In another embodiment, the method may comprise one or more steps preceding any of the steps a, b or c. The method may comprise at least one of automated step, or further comprise at least one automated step.

In some embodiments, e.g. when the target is abundantly expressed in the sample or expressed in a broad dynamic concentration range, it may be preferred that the sample is incubated with one or more binding agents involved in formation single target sites under conditions when the binding agents are capable of forming the target sites with a fractional subpopulation of single target molecules. Embodiments of such conditions are discussed above, In one embodiment, wherein the target does not comprise an inherent oxidoreductase activity and is a low expression target, the target visualization method may be performed as the following:
a) incubating the sample with one or more binding agents, wherein
   (i) at least one binding agent is capable specifically binding to the target;
   (ii) at least one binding agent comprises an enzyme with oxidoreductase activity; and
   (iii) the amount of the binding agent (i) or (ii) is below the value of its dissociation constant (Kd) relating to the binding to its binding partner in the sample,
   thereby forming one or more target sites, wherein a target site comprises a unit of the target and one or more binding agents, wherein at least one of the binding agents comprises the enzyme with peroxidase activity;
b) incubating the sample (a) in an aqueous solution comprising
   i) a first substrate of said enzyme;
   ii) a second substrate of said enzyme, and, optionally,
   iii) a peroxide compound,
   wherein the first substrate is alpha-cyano-4-hydroxycinnamic acid (ACHCA) or a derivative thereof and the second substrate is a conjugate molecule comprising at least one compound that is capable of serving as substrate of the enzyme with peroxidase activity and at least one detectable label;
c) detecting the label of the deposited second substrate at target sites.

As discussed above, the power of the present signal amplification system allows using amounts of binding agents (either the first binding agent or the second binding agent) that are below the value of their Kd relating to the corresponding interaction with their specific binding partner in the sample.

The formation of a binding agent-target complex (C) can be described by a two-state process $$C \rightleftharpoons P+L$$

the corresponding dissociation constant is defined

$$K_d = \frac{[P][L]}{[C]}$$

where [P], [L] and [C] represent molar concentrations of the target (e.g. Protein), binding agent (e.g. Ligand) and complex, respectively.

The dissociation constant has molar units (M), which correspond to the concentration of binding agent [L] at which the binding site on a target (e.g. particular protein) is half occupied, i.e. the concentration of binding agent, at which the concentration of target with binding agent bound [C], equals the concentration of target with no binding agent bound [P]. The smaller the dissociation constant, the more tightly bound the binding agent is, or the higher the affinity between binding agent and target. For example, a binding gent with a nanomolar (nM) dissociation constant binds more tightly to a particular target than a binding agent with a micromolar (μM) dissociation constant.

In the specific case of antibodies (Ab) binding to antigen (Ag), usually the affinity constant is used. It is the inverted dissociation constant.

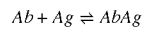
$$Ab + Ag \rightleftharpoons AbAg$$
$$K_a = \frac{[AbAg]}{[Ab][Ag]} = \frac{1}{K_d}$$

This invention provides means to amplify a signal associated with the target site to the extreme. Using reagents and visualization conditions described herein single molecules of even low expression targets may be visualized, detected and counted using standard low-resolution microscopic optics (such as 4×, 10× or 20× magnification bright-field or fluorescence microscopes).

In some procedures for detection of low abundant targets it may be advantageous to use particular binding agents described above. In particular, in one embodiment, it may be preferred to use a single Fab fragment of a polyclonal primary antibody comprising multiple moieties of an enzyme with oxidoreductase activity, e.g. up to 20 HRP. In another embodiment, it may be preferred that the second binding agent is a Fab fragment of a secondary antibody comprising multiple (up to 20) HRP. In another embodiment, it may be preferred to use a second binding agent which is a conjugate molecules comprising a core polymer, such as Dextran, 1-2 specific binding agents and multiple HRP. These reagents are favorable for minimizing unspecific binding of the binding agents in the sample and, simultaneously, for massive labeling of the sites of the sample comprising their specific binding partners with enzyme, enhancing thus the specific deposition of the second substrate at the target sites of the sample. Some examples of these embodiments are described in EXAMPLES.

Any protein or another biological molecule, structure or molecular complex that is known in the art as a biological marker of a disease may be detected at any amounts in a sample of the invention using the above described embodiments, and thus is included in the scope of the invention. In particular, the invention relates to biological markers of cancer.

Accordingly, in one aspect the invention relates to a diagnostic assay comprising a step of visualization and detection of a diagnostic target in a sample in vitro according to the present invention.

As mentioned above, using methods of the invention, multiple targets in the same sample may be visualized and detected simultaneously or sequentially. Flexibility of the system allows visualizing different species of targets or the same target expressed in a broad dynamic range in the sample by using different conjugate molecules (comprising different labels), single molecules of a target or target as the bulk, or a combination of both. All embodiments of the visualization methods described in WO2009036760, WO2010094283, WO2010094284, WO2011047680 and PCT/DK2011/000148 may be directly used or easily adopted for the purposes of the present invention.

In one aspect the invention relates to a method of quantification of a target visualized in a sample according to the methods described herein. Both relative amounts and absolute amounts of targets in samples, in particular in histological samples, may be determined. Generally, a method for quantitative evaluation of an immobilized target in a sample according to the invention comprises:
a) visualizing and detecting a target in the sample according to one of the methods of the invention,
b) quantifying the target in the sample;

Quantification of the target may be done by using traditional stain densitometry-based evaluation, in embodiments wherein the target is visualized as homogenous stain, or it may be done by counting or quantifying distinct dots of color, fluorescence, luminescence or radioactivity in the processed sample, either manually using routine microscopic optics or automatically using image analysis systems considering different features of the dots. The methods for quantification of targets visualized as dots in histological samples are described in detail in PCT/US2011/62424 and PCT/DK2011/000131 and are fully applicable for quantification of a target visualized according to the present invention.

In one embodiment the amount of a target in a sample may be evaluated regardless any reference, e.g. as an amount of the bulk target or a number of single units of a target in the sample. In another embodiment, the amount of a target may evaluated with regard to a reference, e.g. relatively to expression of another object in the sample, such as a biological molecule or cellular structure, relatively to a volume or area of the sample, etc.

The methods as described herein are of particular advantage for the quantitative evaluation of targets in complex histological samples. Accordingly, in one preferred embodiment the invention relates to a quantitative evaluation of a target in histological sample.

Estimation of expression of biological markers, i.e. markers which expression has a diagnostic, prognostic or therapeutic value, is routinely used for making or confirming medical diagnoses or for predicting outcomes of therapeutic treatments, or for monitoring development of diseases. When such evaluation is based on analysis such complex samples as histological samples, it has relative value because the results of analysis are strongly depends on the quality of a sample, sensitivity of the detection method, variations in the expression levels, etc, and therefore evaluation of expression a biological marker in a series of histological samples of same tissue of same patient may give very different results, and lead to an erroneous assumption and diagnosis, and, as a consequence, to non-effective therapy. Evaluation of expression of diagnostic and therapeutic markers based on estimation of the content of single molecules of said markers in patient samples according to the described herein method can provide reliable examination of the samples leading to errorless medical diagnostics and effective personalized target directed therapy.

Accordingly, in one embodiment, methods of the invention may be used in for diagnosing a disease in a patient, wherein said diagnosing comprising a step of evaluation of a biological sample obtained from the patient according to any of the methods of the invention.

In another embodiment, methods of the invention may be used in for estimating efficacy of a therapeutic treatment in a patient, wherein said estimating comprises analysis of a patient sample which has been processed according to any of the methods of the invention.

In another embodiment, methods of the invention may be used for providing a medical prognosis, e.g. a prognosis of the risk of development of a disease in a patient, or prognosis of the likelihood of recovery or failure form a disease, wherein a method of said prognosis comprises a step of processing and analysis of a biological sample obtained from a patient according to any of the methods of the invention.

In another embodiment, methods of the invention may be used for stratification of patients for a therapeutic regime, wherein said stratification comprising analysis of samples of patients which have been processed according to any of the method of the invention.

The method may also be used for monitoring a disease, e.g. disease progression or amelioration, or can also be used in the process of new drug screening, e.g. for estimating a therapeutic potential of a new drug in an in vitro assay, etc.

Visualization methods of the invention may be employed in a variety assay formats that typically used for latter applications, e. g flow cytometry (FC), ELISA, histochemistry (both IHC and ISH), blotting, etc. For example, in one embodiment the biological sample may be a suspension of cells. Target biological molecules or target structures of cells in suspension may be detected using FC, ELISA, IHC or ISH. When ELISA, IHC or ISH are used for the detection, cells of a suspension are to be attached to a solid support, e.g. a plate (ELISA) or a slide (IHC). In another embodiment the biological sample may be a sample of a body tissue, e.g. a section of a fixed and paraffin embed tumor sample. Target molecules or structures of cells of such samples will be typically detected using IHC or ISH.

IHC and ISH assay formats usually require a series of treatment steps preceding visualization of target molecules which may be conducted on a tissue section mounted on a suitable solid support for microscopic inspection, or the production of photomicrographs, e.g., a glass slide or other planar support, to highlight by selective staining certain morphological indicators of disease states or detection of biological markers. Thus, for example in IHC, a sample is first taken from an individual, then fixed and only then it exposed to antibodies which specifically bind to the biological marker of interest. The sample processing steps may also include other steps preceding a visualization procedure according to the invention, for example, It may involve the steps of: cutting and trimming tissue, fixation, dehydration, paraffin infiltration, cutting in thin sections, mounting onto glass slides, baking, deparaffination, rehydration, antigen retrieval, blocking steps, etc., Washing steps may be performed with appropriate buffers or solvents, e.g., phosphate-buffered saline (PBS), tris buffered saline (TBS), distilled water. The wash buffers may optionally contain a detergent, e.g., Tween 20. All these procedures are well-known routine procedures in laboratories.

Both of two categories of histological samples: (1) preparations comprising fresh tissues and/or cells, which generally are not fixed with aldehyde-based fixatives, and (2) preparations of fixed and embedded tissue specimens, often archived material, may be processed using methods of the invention.

Many methods of fixing and embedding tissue specimens are known, for example, alcohol fixation and formalin-fixation and subsequent paraffin embedding (FFPE). Fixatives are needed to preserve cells and tissues in a reproducible and life-like manner and immobilize targets in the samples. To achieve this, tissue blocks, sections, or smears are immersed in a fixative fluid, or in the case of smears, are dried. Fixatives stabilize cells and tissues thereby protecting them from the rigors of processing and staining techniques and immobilize targets wilting the sample protecting target lost during further procedures.

Any suitable fixing agent may be used, for example, ethanol, acetic acid, picric acid, 2-propanol, tetrahydrochloride dihydrate, acetoin (mixture of monomer and dimer), acrolein, crotonaldehyde (cis+trans), formaldehyde, glutaraldehyde, glyoxal, potassium dichromate, potassium permanganate, osmium tetroxide, paraformaldehyde, mercuric chloride, tolylene-2,4-diisocyanate, trichloroacetic acid, tungstic acid. Other examples include formalin (aqueous formaldehyde) and neutral buffered formalin (NBF), glutaraldehyde, acrolein, carbodiimide, imidates, benzoequinone, osmic acid and osmium tetraoxide.

Fresh biopsy specimens, cytological preparations (including touch preparations and blood smears), frozen sections and tissues for immunohistochemical analysis are commonly fixed in organic solvents, including ethanol, acetic acid, methanol and/or acetone.

To facilitate the specific recognition in fixed tissue, it is often necessary to retrieve or unmask the targets, i.e., the biological markers of interest, through pre-treatment of the specimens to increase reactivity of the majority of targets. This procedure is referred to as "antigen retrieval", "target retrieval" or "epitope retrieval", "target unmasking" or "antigen unmasking." An extensive review of antigen retrieval (antigen unmasking) may be found in Shi et al. 1997, *J Histochem Cytochem,* 45(3):327.

Antigen retrieval includes a variety of methods by which the availability of the target for interaction with a specific detection reagent is maximized. The most common techniques are enzymatic digestion with a proteolytic enzyme (for example proteinase, pronase, pepsin, papain, trypsin or neuraminidase) in an appropriate buffer or heat induced epitope retrieval (HIER) using microwave irradiation, heating in a water bath, a steamer, a regular oven, an autoclave or a pressure cooker in an appropriately pH stabilized buffer, usually containing EDTA, EGTA, Tris-HCl, citrate, urea, glycin-HCl or boric acid. Detergents may be added to the HIER buffer to increase the epitope retrieval or added to the dilution media and/or rinsing buffers to lower non-specific binding.

The antigen retrieval buffer is most often aqueous, but may also contain other solvents, including solvents with a boiling point above that of water. This allows for treatment of the tissue at more than 100° C. at normal pressure.

Additionally, the signal-to-noise ratio may be increased, if desired, by different physical methods, including application of vacuum and ultrasound, or freezing and thawing of the sections before or during incubation of the reagents.

Endogenous biotin binding sites or endogenous enzyme activity (for example phosphatase, catalase or peroxidase) may be removed as a pre-detecting step in the detection procedure, e.g., endogenous biotin may be blocked by pretreatment of the sample with streptavidin, and peroxidase activity may be removed by treatment with peroxides. Endogenous phosphatase activity may be removed by treatment with levamisole. Endogenous phosphatases and esterases may be destroyed by heating. Other methods of such pretreatment known in the art may also be used.

Blocking of non-specific binding sites is not necessary when the methods of the present invent are used, however, if desired, blocking may be performed using standard approached of the art, e.g. with inert proteins like, horse serum albumin (HSA), casein, bovine serum albumin (BSA), and ovalbumin, fetal calf serum or other sera, or detergents like Tween20, Triton X-100, Saponin, Brij or Pluronics may be used. Blocking non-specific binding sites in the tissue or cells with unlabeled and target non-specific versions of the specific reagents may also be used.

Samples may also be prepared and target molecules detected using the free floating technique. In this method a tissue section is brought into contact with different reagents and wash buffers in suspension or freely floating in appropriate containers, for example micro centrifuge tubes.

The tissue sections may be transferred from tube to tube with different reagents and buffers during the staining procedure using for example a "fishing hook like" device, a spatula or a glass ring. The different reagents and buffer can also be changed by gentle decantation or vacuum suction. Alternatively, containers with the tissue sections can be emptied into a special staining net, like the Corning "Netwells" (Corning) and the tissue section washed before being transferred back into the tube for the next staining step.

All the steps, including for example fixation, antigen retrieval, washing, incubation with blocking reagents, immuno-specific reagents and the oxidoreductase-mediated deposition, are done while the tissue section is floating freely or withheld on nets. After deposition of the reporter, the tissue section is mounted on slides, the reporter is detected and slide covered with a cover slip before being analyzed, e.g., by light or fluorescent microscopy.

In some embodiments, the tissue section may be mounted on slides following the critical incubation with the immunospecific reagents following the procedure (a) of the method. The rest of the process of detection is then conducted on the slide mounted tissue sections.

Any of the assays employing the methods of the invention may comprise one or more automated steps. In one embodiment the assays may comprise a manual detection, in another embodiment the assays may be fully automated, in another embodiment the assays may be adjusted for a semi-automated detection.

EXAMPLES

The following are non-limiting working example of the disclosed invention.

Abbreviations

MBHA 4-Methylbenzhydrylamine
NMP N-Methyl Pyrolidon
HATU 2-(1h-7-azabenzotriazole-1-yl)-1,1,3,3 tetramethyl uronium hexafluorophosphate; methenamminium
DIPEA Diisopropyl EthylAmine
DCM Dichloro Methane
TFA TriFluoroacetic Acid
TFMSA TriFluor Methyl Sulphonic Acid
Flu Carboxy-fluorescein
Dex Dextran
HPLC High Performance Liquid Chromatography
equi. Equivalent
L30 1,10,16,25-tetraaza-4,7,13,19,22,28-hexaoxa-11,15,26,30-tetraoxo-triacontane
L60, L90, L120, L150 different polymers of L30, comprising 2, 3, 4 or 5 L30 repeats
ClZ 2-chloroZ=2chloro Benzyloxycarbonyl
FITC FloresceinIsoThioCyanate
HRP Horse Radish Peroxidase
GaM Goat anti-Mouse antibody
DNP 2,4 dinitro-fluorbenzene (DiNitroPhenyl)
LPR Liquid Permanent Red (Dako K0540)
ACin 4-aminocinnamic acid
Sin sinapinic acid (4-hydroxy-3,5-dimethoxycinnamic acid)
Caf caffeic acid (3,4-dihydroxycinnamic acid)
Fer ferulic acid (3-methoxy-4-hydroxycinnamic acid)
PNA-X peptide nucleic acid oligomer (N-(2-aminoethyl)-glycine) comprising different substituents coupled to the central nitrogen
A adenine-9-acetic acid,
C cytosine-1-acetic acid,
D 2,6-diaminopurine-9-acetic acid, G guanine-9-acetic acid,
Gs 6-thioguanine-9-acetic acid,
P 2-pyrimidinone-1 acetic acid,
T thymine-1-acetic acid,
Us 2-thiouracil-1-acetic acid.
Dpr 2,3 diamino-propioninc acid,
Phe phenylalanine,
Tyr tyrosine,
Trp tryptophane,
Lys lysine,
Cys cysteine,
betaala betaalanine, N,N diacetic acid
FFPE formaldehyde fixed paraffin embedded
SMD single molecule detection
Cross-linker the first substrate of an enzyme with oxidoreductase activity
Reporter the second substrate with an enzyme with peroxidase activity
ACHCA alpha-cyano-4-hydroxycinnamic acid
Conjugate Molecules

TABLE 1

Conjugate molecules, intermediate products of their synthesis and control constructs

| | Conjugate ID | Structure | Synthesis protocol No. |
|---|---|---|---|
| 1 | D19112/D19057 | Fer-Lys(Fer)-Lys(Fer)-L150-Lys(Flu) | 2 |
| 2 | D19185/D20068/ D20171/D20166/ D21025/D21030/ D21032/D21045/ Reporter 1 | Fer-Lys(Fer)-Lys(Fer)-Lys(Fer)-L150-Lys(Flu) | 2 |
| 3 | D20086 | Fer-Lys(Fer)-Lys(Fer)-L30-Lys(Flu) | 2 |
| 4 | D20118 | Fer-Lys(Fer)-Lys(Fer)-L60-Lys(Flu) | 2 |
| 5 | D20120 | Fer-Lys(Fer)-Lys(Fer)-Glu-L30-Lys(Flu) | 2 |
| 6 | D19048/D21053/ Reporter 2 | Fer-Lys(Fer)L150-Lys(Lissamine) | 2 |
| 7 | D19059 | Fer-Lys(Fer)-Lys(Fer)-L150-Lys(DNP) | 2 |
| 8 | D18146 | ACin-(Lys(ACin)L30)$_5$-(L90-Lys(Flu))$_3$ | 2 |
| 9 | D18044 | Ac-(Tyr-L30)$_5$-(L90-Lys(Flu))$_3$ | 1 |
| 10 | D21008 | (D18074)$_{18.5}$-Dex70-(D18118)$_{27.7}$ | 8 |
| 11 | D18074/D17120/ D17137/D18114 (intermediate) | Fer(Lys(Fer)-L30)$_5$-Lys(NH$_2$) | 3 |
| 12 | D21020 | Caf-Lys(Caf)-Lys(Caf)-L150-Lys(Flu) | 2 |
| 13 | 0328-018/ D21047/D21067 | Sin-Lys(Sin)-Lys(Sin)-L150-Lys(Flu) | 2 |
| 14 | D17093 intermediate | Fer(PNA-Fer)5L30-Lys(NH2) | 3 |
| 15 | D17127/D18118 intermediate | NH2-Cys(SH)-L90Lys(Flu)-L90-Lys(Flu)-L90-Lys(Flu) | 1 |
| 16 | D17128 | (D17093)$_{18.6}$-Dex70-(D17127)$_{26.2}$ | 8 |
| 17 | D17130 | (D17120)$_{18.8}$-Dex70-(D17127)$_{18.6}$ | 8 |
| 18 | D17132 control (no enzyme substrate) | Dex70-(D17127)$_{23}$ | 7 |
| 19 | D17126/D17165 intermediate | Betaala-L90-Lys(Flu)-L90-Lys(Flu)-L90-Lys(Flu) | 1 |
| 20 | D17134/D17135/ D17136 | Fer(Lys(Fer)-L30)5-Lys-(betaala)-(L90-Lys(Flu))3 | 6 |
| 21 | D17138 | Fer(Lys(Fer)-L90)$_5$-Lys(NH$_2$) | 3 |
| 22 | D17139 | Fer-Lys(Fer)L30-(Lys(Fer))2-L30(Lys(Fer))2L30-Lys(NH2) | 3 |
| 23 | D17140 | Fer-Lys(Fer)L60-(Lys(Fer))2-L60(Lys(Fer))2L30-Lys(NH2) | 3 |
| 25 | D17148/D17150/ D17151 | Fer-Lys(Fer)-(L30-Lys(Fer)-Lys(Fer))2-L30-Lys-(betaala)-(L90-Lys(Flu))3 | 6 |
| 24 | D17152 | Fer-L30-Lys(L30Fer)-(L30Lys(L30Fer))4-L30-Lys(NH2) | 5 |
| 26 | D17156 | Fer-L30-Lys(L30Fer)-(L30Lys(L30Fer))4-L30-Lys(betaala)-(L90-Lys(Flu))3 | 6 |
| 27 | D17157 | Fer-L150-Lys(Flu) | 2 |
| 28 | D17158 | Fer-L30-Lys(Flu) | 2 |
| 29 | D17161 control (no enzyme substrate) | Flu-L150-Lys(Flu) | 1 |
| 30 | D17162 control (no enzyme substrate) | Dex270-(D17127)$_{62.9}$ | 7 |
| 31 | D17104 intermediate | Fer-(Lys(Fer)-Gly)4-Lys(Fer)-L30-Lys(NH2) | 3 |
| 32 | D17188 | Fer-(Lys(Fer)-Gly)4-Lys(Fer)-L30-Lys(betaala)-(L90-Lys(Flu))3 | 6 |
| 33 | D17192 intermediate | 7-OH-Cou-(Lys(7-OH-Cou)-L30)5-Lys(NH2) | 3 |
| 34 | D18003 | 7-OH-Cou-(Lys(7-OH-Cou)-L30)5-Lys(betaala)-(L90-Lys(Flu))3 | 6 |

TABLE 1-continued

Conjugate molecules, intermediate products of their synthesis and control constructs

| | Conjugate ID | Structure | Synthesis protocol No. |
|---|---|---|---|
| 35 | D18007 control (no enzyme substrate) | Ac-(PNA-D)5-L120-Lys(Flu)-L90-Lys(Flu)-L90-Lys(Flu) | 1 |
| 36 | D18008 control (no enzyme substrate) | Ac-(PNA-G)5-L120-Lys(Flu)-L90-Lys(Flu)-L90-Lys(Flu) | 1 |
| 37 | D18009 control (no enzyme substrate) | Ac-(PNA-Gs)5-L120-Lys(Flu)-L90-Lys(Flu)-L90-Lys(Flu) | 1 |
| 38 | D18010 control (no enzyme substrate) | Ac-(PNA-P)5-L120-Lys(Flu)-L90-Lys(Flu)-L90-Lys(Flu) | 1 |
| 39 | D18011 control (no enzyme substrate) | Ac-(PNA-A)5-L120-Lys(Flu)-L90-Lys(Flu)-L90-Lys(Flu) | 1 |
| 40 | D18012 control (no enzyme substrate) | Ac-(PNA-C)5-L120-Lys(Flu)-L90-Lys(Flu)-L90-Lys(Flu) | 1 |
| 41 | D18013 control | Ac-(PNA-T)5-L120-Lys(Flu)-L90-Lys(Flu)-L90-Lys(Flu) | 1 |
| 42 | D18014 control (no enzyme substrate) | Ac-(PNA-Us)5-L120-Lys(Flu)-L90-Lys(Flu)-L90-Lys(Flu) | 1 |
| 43 | D18015/D18126/D19130 | Fer-(Lys(Fer)-L30)5-(L90-Lys(Flu))3 | 2 |
| 44 | D18019/D18029 intermediate | Fer-(Lys(Fer)-L30)5-L270-Lys(NH2) | 3 |
| 45 | D18031 | (D18019)$_6$-Dex70-(D17127)$_{22.3}$ | 8 |
| 46 | D18049 | Ac-(Tyr)6-L30-(L90Lys(Flu))3 | 1 |
| 47 | D18077 similar to D17130 | (D18074)$_{17.8}$-Dex70-(D17127)$_{22.2}$ | 8 |
| 48 | D18079 similar to D17130 | (D18074)$_{16.8}$-Dex70-(D17127)$_{23}$ | 8 |
| 49 | D18080/19028 intermediate | Fer-(Lys(Fer)-L30)5-(L90-Lys(NH2))3 | 3 |
| 50 | D18081 | Fer-(Lys(Fer)-L30)5-(L90-Lys(Texas-Red-X))3 | 4 |
| 51 | D18084 | NH2-Dpr(NH2)-(L30-Tyr)7 | 1 |
| 52 | D18085 | NH2-Dpr(NH2)-(L90-Lys(Flu))3 | 1 |
| 53 | D18086 control (no enzyme substrate) | Dex70(D18085)$_{2.6}$ | 7 |
| 54 | D18088 control (no enzyme substrate) | Dex70-(D17127)$_{8.6}$ | 7 |
| 55 | D18090 similar to D17130 | (D18074)$_{16.8}$-Dex70-(D17127)$_{23.9}$ | 8 |
| 56 | D18096 | Fer-(Lys(Fer)-L30)5-(L90-Lys(7-OH-Cou))3 | 4 |
| 57 | D18122 | (D18114)$_{17.6}$-Dex70-(D18118)$_{32.9}$ | 8 |
| 58 | D18128 | NH2-Cys(SH)-(L30-Tyr)5-(L90Lys(Flu))3 | 1 |
| 59 | D18130 | Dex70-(D18128)$_{12.4}$ | 7 |
| 60 | D18132 | NH2-Cys(SH)-(Tyr)5-(L90Lys(Flu))3 | 1 |
| 61 | D18133 | Dex70-(D18132)$_{21.8}$ | 7 |
| 62 | D18137 | Ac-(Tyr)5-(L90Lys(Flu))3 | 1 |
| 63 | D18138 | Ac-(Tyr)5-(L90Lys(DNP))3 | 1 |
| 64 | D18141/D18155/D19032 | Fer-(Lys(Fer)-L30)5-(L90-Lys(DNP))3 | 2 |
| 65 | D18157 | Fer-(L30-Lys(Fer))5-(L90-Lys(Flu))3 | 2 |
| 66 | D19037 | Fer-Lys(Fer)-L150-Lys(Flu) | 2 |
| 67 | D19040/D19046 | Fer-Lys(Fer)-L150-Lys(DNP) | 2 |
| 68 | D21028 | Sin-Lys(Sin)-Lys(Sin)-Lys(Sin)-L150-Lys(Flu) | 2 |
| 69 | D21048 | Sin-Lys(Sin)-Lys(Sin)-L150-Lys(DNP) | 2 |
| 70 | D21150 | Sin-Lys(Sin)-Lys(Tyr)-L150-Lys (Flu) | 2 |

Different conjugates and their intermediate compounds are classified in column 3 of the table according to methods of their synthesis, roughly in increasing order of complexity:

1. Solid phase chemistry only.
2. Solid phase, then one solution phase step.
3. Solid phase, then two solution phase steps.
4. Solid phase, then two solution phase steps
5. Solid phase, then four solution phase steps.
6. Solution phase coupling between amino and betaalaanhydride intermediates.
7. Dextran conjugates with one substituent.
8. Dextran conjugates with two substituents.

1. This group includes the 8 conjugates prepared from Tri-Fluorescein labeled PNA-pentamers of the 4 natural and further 4 unnatural bases. (D18007-D18014). There are 4 tyrosin conjugates with 5-6 tyrosines and 3 fluoresceins, D18044, D18049, D18137 and D18138 with three DNPs in place of fluorescein labels. D18128 and D18132 have 5 tyrosines and 3 fluoresceins each, and as such they are potential conjugates, though they also include an N-terminal cystine residue for further dextran coupling, bringing them into the group of "intermediates". Intermediates further include the important Cysteine (D17127) and betaalnine (D17126) tri-fluorescein linkers, as well as the Diaminopropionic-acid linker with 7 tyrosines (D18084) or three fluoresceines (D18085). Finally the small di-fluorescein linker (D17161) used as control was also prepared by solid phase synthesis alone. The synthetic strategy behind all these compound is simple: Boc-protected monomers are commercially available or have prepared in house, and the conjugates and intermediates are prepared by linear solid phase syntheses, followed by cleavage from resin by a cocktail of 6:2:1:1 TFMSA:TFA:m-cresol:thioanisol. For the best results consequent double coupling of all monomers is used. Fluoresceins are introduced on lysine side chains (and the N-terminal, D17161) following Fmoc-deprotection on solid phase. HATU activated Carboxy-fluorescein (mixed isomers) was used for fluorescein labeling (0.2 M in NMP for 3×20 min). DNP labeling was achieved with 2,4-dinitrofluor-benzene (0.5 M in NMP with DIPEA for 2×10 min).

2. This group includes a large number of conjugates labeled with cinnamic acid derivatives in solution phase following solid phase synthesis of intermediates carrying free N-terminal amino groups and free lysine side chains amino groups. Alpha-N-Boc-(epsilon-N-2-Cl—Z)-lysine was used to introduce lysine residues giving free epsilon-N-amino groups following cleavage from resin. The solution phase labeling is basically an extension of solid phase techniques, utilizing that the relative high molecular weight intermediates can be almost quantitatively precipitated with diethyl ether from TFA or NMP solution.

3. From a synthetic point of view, this group of intermediates represents a yet higher degree of complexity. Solid phase synthesis and solution phase labeling as in 1 and 2, then followed by an additional step of solution phase Fmoc-deprotection. By combining Boc-L30 linkers with Boc-2ClZ and Boc-Fmoc-lysine, intermediates with a combination of protected (Fmoc) lysine side chains and free N-terminal and other lysine side chain free amino groups (from N-terminal Boc and 2-ClZ lysine residues during resin cleavage). These intermediate can be labeled with ferulic acid in solution as in 2. However, prior to the scrubbing step with ethylenediamine, an extra 5 min step with 5% ethanolamine is used. This extra scrubbing step deactivates amino reactive species prior to Fmoc de-protection by ethylenediamine. Without this extra step, ethylenediamine de-protects Fmoc-groups faster than it deactivates HATU activated ferulic acid, and Fmoc "protected" amino groups become labeled with ferulic acid. This group with free amino groups comprises D17120 (six ferulic acids) D17093 (five ferulic acids attached to PNA backbone), D17138 (L90-linkers between ferulic acids) D17139 (six ferulic acids in three close pairs), D17104 (glycine spacers between ferulic acids) D17192 (with six 7-hydroxy coumarins instead of ferulic acids), D18019 (extended L270 linker between closest ferulic acid and free amino group), D18080 (three free amino groups with L90 spacing).

4. From the intermediate D18080 with six ferulic acids and three free amino groups two conjugates were prepared by further solution phase labeling. D18081 with three Texas-Red-X's and D18096 with three 7-hydroxy coumarins. This illustrates how conjugates can be labeled in solution with two different substituents. The advantage is that the intermediate D18080 can be purified prior to the final labeling, an advantage when using labile or expensive labels such as Texas Red.

5. The synthesis of D17152 illustrates the extent of solid phase synthesis chemistries that can be applied to linkers in solution, followed by repeated precipitation by diethyl ether to remove low molecular weight reactants and solvents: On solid phase NH2-Lys(NH2)-(L30-Lys(NH2))4-L30-Lys (Fmoc) was prepared and cleaved from the resin. Boc-L30 linkers were then coupled to the six free amino groups in solution. The intermediate was precipitated and dissolved in 5% m-cresol in TFA twice. Then ferulic acid labeling was performed as in 2 on the now L30 extended amino groups, followed by ethanolamine and ethylenediamine scrubbing as in 3 and finally 3 TFA precipitations as in 1.

6. Fragment couplings were carried out between amino substituted intermediates and "betaalaanhydride" activated intermediates. D17126 with three fluoresceins further carries an N-terminal betaalanine-N,N-diacetic acid. By activation (NMP:diisopropyl carbodiimide:pyridine; 88:10:2) for 10 min a cyclic "betaalaanhydride" is formed that can be used for coupling to amino groups. This gave D17134 (six ferulic acids with L30 spacing) from D17120, D17148 (six ferulic acids in three pairs with L30 spacing) from D17139, D17156 (six L30 extended ferulic acids) from D17152 and D18003 (with six 7-hydroxy coumarins) from D17192. The advantage of such fragment coupling is that intermediates can be HPLC purified prior to coupling, affording large and complex, yet quite pure conjugates. Another advantage is that a single intermediate as D17126 can be used to prepare a series of related, but different conjugates.

7. Dextran conjugates with a single substituent includes the control fluorescein-only conjugates D17132, D18130 and D18088 (all Dex70 conjugates from D17127 via cystein coupling), D17162 (dex270 conjugate from D17127) and D18086 (from D18085 with less efficient coupling via diamino proprioninc acid). These were used as controls to demonstrate that fluorescein-only conjugates did not work. Conjugates were also prepared this way, by coupling multiple intermediate conjugates to dextran. These include D18133 (dex 70 with L30 spaced tyrosine-fluorescein conjugate D18132) and D18130 (dex 70 with tyrosine-fluorescein conjugate D18128. The advantage of coupling a single conjugate with both HRP substrates and labels, is that a fixed ratio between the two substituents is assured.

8. Dextran conjugates with two different substituents include D17130, D18077, D18079, D18090, D18122 and D21008 that are all dex70 with six ferulic acid linker D18074 and tri-fluorescein linker D17127 (or reproductions of linkers). There was good reproducibility between D17130, D18077, D18079 and D21008 with around 100 ferulic acids and 70 fluoresceins, whereas D18122 was coupled with further excess of fluorescin linker to give a conjugate with approx 100 ferulic acids and fluoresceins each. D17128 resembles D17130, but the ferulic acid linker used (D17093) has ferulic acids attached to PNA backbone rather than lysine side chains. The conjugate D18031 is also with D17127, but with the L270 extended ferulic acid linker D18019. This conjugate was an attempt to make ferulic acids more readily accessible to HRP enzymes.

Examples of Synthesis Procedures for Selected Compounds of the Table

D19185: Boc-(Lys(2-Cl—Z))3-L150-Lys(Fmoc) is prepared on solid phase. The Fmoc group is removed, followed by fluorescein labeling as described above. The intermediate NH2-((Lys(NH2))3-L150-Lys(Flu) results from cleavage from resin. It is precipitated with diethyl ether, dissolved in TFA, precipitated then dissolved in NMP and made basic with DIPEA. This solution is mixed with an equal volume of 0.2 M ferulic acid in NMP activated by HATU and DIPEA. After 10 min the labeling is complete and the crude product is further "scrubbed" by addition of ethylene diamine to a concentration of 10% for 5 minutes. Following precipitation with diethyl ether, the product is further dissolved in TFA and precipitated with diethyl ether three times to remove low molecular weight debris. Prior to "scrubbing" with ethylene diamine, mass spectroscopy shows two kinds of adducts (and combinations thereof): +(176)n indicating extra ferulic acids (phenolic esters on other ferulic acids and fluorescein) and +98 (N,N'-tetramethyl uronium adducts, likewise on unprotected phenolic groups). These are completely removed by the ethylene diamine treatment, and active esters and ferulic acid oligomers are likewise decomposed.

The following fluorescein-Ferulic acid conjugates were made according to this scheme: D17157, D17158, D19112, D19185, D18015, D20086, D20118, D20120, D19037 and D18157 (detailed synthesis some of these conjugates is described below). Ferulic acid conjugates with other labels include: D19048 (lissamine labeled); D19059, D18141 and D19040 (DNP labeled). Conjugates with sinnapinic acid in place of ferulic acid were prepared by the same methodology and include 0328-018 and D21028 with fluorescein labels and the DNP labeled D21048. D21020 is with is with three caffeic acids and a fluorescein, D18146 with six 4-amino-cinnamic acids and three fluoresceins and are both prepared by the same strategy.

D17158 MBHA resin was downloaded with Fmoc-Lys (ivDDE) to a loading of 150 micro mol/g. 200 mg resin was de-Fmoc'ed with 20% piperidine in NMP, the subjected to one coupling with Boc-L30-OH (1.5 mL 0.26 M in NMP, preactivated with 0.9 equi. HATU, 2 equivalents DIPEA for 2 min) for 20 min. The ivDDE group was removed with 5% hydrazine in NMP, and the lysine side chain was labelled with carboxy fluorescein (Flu) (1.5 mL 0.2 M in NMP, preactivated for 2 min with 0.9 equi. HATU, 2 equi DIPEA) for 2×20 min. The resin was treated with 20% piperidine in NMP, NMP, DCM then DCM. The intermediate product H-L30-Lys(Flu)-NH$_2$ was cleaved, of the resin with TFA: TFMSA:mCresol (7:2:1, 1.5 ml for 1 h), precipitated with diethyl ether, re-suspended in TFA, precipitated with diethyl ether, re-suspended in NMP and again precipitated with diethyl ether. It was made basic with 100 microL DIPEA and dissolved directly in 0.5 mL 0.3M Ferulic acid preactivated with 0.9 equi. HATU and 2 equi. DIPEA. After 25 min the crude product was precipitated with diethyl ether, dissolved in 450 microL NMP and 50 microL ethylenediamine. After 5 min the product was precipitated with diethyl ether, dissolved in 15% acetonitril in water (8 mL) and acidified with 100 microL TFA and subjected to RP-HPLC purification.

D17157 MBHA resin was downloaded with Boc-Lys (Fmoc) to a loading of 100 micro mol/g. 100 mg resin was subjected to 5 coupling cycles with Boc-L30-OH (a. Coupling with Boc-L30-OH as in 1. b. Capping with 2% acetic anhydride in NMP:Pyridine 1:1, 2 min. c. De-Bc with 5% mCresole in TFA 2×5 Min.). The lysine side chain was De-Fmoc'ed and labelled with carboxy fluoresceine, as in 1. The intermediate product H-L150-Lys(Flu)-NH$_2$ was cleaved of the resin, and labelled N-terminally with Ferulic Acid and purified as in 1.1.

D16127 Boc-L90-Lys(Fmoc)-L90-Lys(Fmoc)-L90Lys (Fmoc) was prepared on 0.5 g MBHA resin with standard solid phase chemistry (as in 1.1. and 1.2). Fmoc groups were removed from lysine side chains with 20% piperidine in NMP and the compound was subjected to repeated carboxy fluorescein labelling (3×30 min). Following removal Boc groups with TFA, the N-terminal was labeled on solid phase with betaalanine-N,N-di acetic acid (betaala) tert-butyl ester. Following cleavage from resin and HPLC purification, betaala-L90-Lys(Flu)-L90Lys(Flu)-L90-Lys(Flu)-NH2 was isolated.

D17127 Boc-L90-Lys(Fmoc)-L90-Lys(Fmoc)-L90Lys (Fmoc) resin was prepared and labeled with fluorescein using the procedure described in 1.3. Following removal Boc groups the N-terminal was labeled with N-Boc-S(4-Methoxybenzyl)-Cys-OH. The compound was cleaved from the column and purified by HPLC:

D18074/D17128 To MBHA resin was sequentially coupled Boc-Lys(Fmoc) (2 cycles), Boc-L30-OH (5 cycles) and Boc-Lys(2ClZ)—OH. The intermediate product was cleaved from the resin in the presence of 10% thioanisol scavenger to remove 2ClZ-groups. The N-terminal and the 5 de-protected lysine side chains were labeled with Ferulic acid as in 1.1 (2×30 Min). The Fmoc group on the N of the C-terminal Lysine residues was then removed with 10% ethylene diamine in NMP prior to purification.

D17134 betaala-L90-Lys(Flu)-L90Lys(Flu)-L90-Lys (Flu)-NH2 (D16126) (see 1.4 above) 500 nmol was dissolved in 88 microL NMP and 2 microL pyridine, and converted to cyclic anhydride by reaction with 10 microL diisopropyl carbodiimide for 10 min. The anhydride was precipitated with diethyl ether, and the pellet was dissolved in 100 microL NMP comprising 250 nmol Fer-(Fer-L30)$_5$-Lys(NH$_2$)—NH$_2$. After 20 min 5 microL ethylene diamine was added, and after 5 min the product was precipitated with diethyl ether, acidified and HPLC purified.

D18044 Ac-(Tyr(2BrZ)-L30)$_6$-L90-Lys(Fmoc)-L90-Lys (Fmoc)-Lys(Fmoc) was prepared on MBHA resin. On solid phase the Fmoc groups were removed, and the lysine side chains labeled with carboxy fluorescein. Following cleavage from the resin, the product was HPLC purified.

D17140 Boc-Lys(2ClZ)-L60-Lys(2ClZ)-Lys(2ClZ)-L60-Lys(2ClZ)-Lys(2ClZ)-L30-Lys(Fmoc) was prepared on MBHA resin. Following cleavage from the resin, the intermediate product H-Lys(NH$_2$)-L60-Lys(NH$_2$)-Lys(NH$_2$)-L60-Lys(NH$_2$)-Lys(NH$_2$)-L30-Lys(Fmoc) was isolated by precipitation, and labeled with Ferulic acid as in 1.1. The final product was isolated by HPLC.

D18090 Dextran MW 70 kDa, activated with divinyl sulphone, 10 nmol, was reacted with Fer-(Fer-L30)$_5$-Lys(NH$_2$)—NH$_2$ (D18074) (see (see 1.4 above). 500 nmol, in a total volume of 300 microL 0.16M NaHCO$_3$ pH 9.5 for 30 min at 40 C. After a slight precipitation was observed, further 100 microL water was added and the reaction was allowed to proceed for another 30 min. Further 200 microL 0.15 M NaHCO$_3$ was added together with 500 nmol H-Cys-L90-Lys(Flu)-L90Lys(Flu)-L90-Lys(Flu)-NH2 (D17127) (see 1.5 above). After 1 h at 40 C, the reaction mixture was quenched by addition of 50 microL 0.165M cystein for 30 min, solution was filtered, and the product was purified by FPLC on superdex 200 with 20% EtOH in aqueous solution containing 10 mM CHES, pH 9.0, and 0.1 M NaCl. The product eluted was a Dextran conjugate comprising around 56 Fluorescein and 113 Ferulic Acid residues.

D19112 On solid phase MBHA resin Boc-Lys(2Clz)-Lys (2ClZ)-L150-Lys(Fmoc) was prepared using standard solid phase Boc chemistry. The Fmoc group was removed using 20% piperidine in NMP (2×5 min), and the free amino group was labeled with carboxy fluorescein (0.2 M carboxy fluorescein activated with 0.9 equi.HATU and 1 equi. DIPEA in NMP for 3 times 20 min). The resin was then subjected to treatment with 20% piperidine in NMP for 2×5 min. Cleavage from the resin was performed in TFA:TFMSA:m-cresole:thioanisole (6:2:1:1) mixture for one hour and resulted in the intermediate product H2N-Lys(NH2)-Lys(NH2)-L150-Lys(Flu). This product was dissolved in TFA, precipitated with diethyl ether, and then dissolved in NMP and again precipitated with diethyl ether. The precipitate was then dissolved in 0.3 M ferulic acid activated with 0.9 equivalents HATU and two equivalents Diisopropyl-ethylamine. After 10 min reaction, the product was precipitated with diethyl ether and then dissolved in 10% ethylenediamine in NMP for 2 min. The final product was then precipitated with diethyl ether, dissolved in 30% acetonitrile in water and HPLC purified on a C18 column.

D19185, D20068 and D20171 were prepared in the same way as D19112, with the introduction of an additional Lys(Fer) group.

D21020: Caf-Lys(Caf)-Lys(Caf)-L150-Lys(Flu), was prepared as D19185. Following solid phase synthesis, caffeic acid labeling was performed in solution.

0328-018: Sin-Lys(Sin)-Lys(Sin)-L150-Lys(Flu) was prepared as D19185. Following solid phase synthesis, sinapinnic acid labeling was performed in solution D20118: was prepared in the same way as D19112, using L60 linker.

D20086: was prepared in the same way as D19112, using L30 linker.

D20120: was prepared in the same way as D19112, using L30 linker, and, additionally, a glutamic acid residue. Boc-Glu(O-benzyl) was used for solid phase synthesis to build in the glutamic acid residue.

D19048: On 0.5 g MBHA resin Boc-L$_{150}$-Lys(Fmoc) was prepared. The Fmoc group was removed and the lysine side chain amino group was labeled with Lissamin (Molecular Probes product nr. L20, rhodamine B sulphonyl chloride) using 100 mg in 2 mL NMP with addition of 80 microL DIPEA for 3 times 10 min. The Boc group was then removed with TFA, and Boc-Lys(2ClZ) was coupled to the N terminal. The intermediate product H$_2$N-Lys(NH$_2$)-L150-Lys(Lissamine) was cleaved from the resin with TFA:TFMSA:m-cresole:thioanisole (6:2:1:1) and labeled with ferulic acid as described for D19112 to give Fer-Lys(Fer)-L150-Lys(Lissamin). The product was purified by RP-HPLC, splitting into two separate peaks representing different isomers of Lissamine. The first isomer turned almost colorless in basic aqueous solution, and was discharged. The second isomer retained color and fluorescence in basic aqueous solution and was collected.

D19059: was prepared in the same way as D19112, but labeled on the C-terminal lysine side chain amino group on solid phase with DiNitroPhenyl using 100 mg 2,4-dinitrofluorobenzen in 1.5 mL NMP with addition of 50 microL DIPEA for 2 times 20 min.

D18126: Fer-Lys(Fer)-L30-Lys(Fer)-L30-Lys(Fer)-L30-Lys(Fer)-L30-Lys(Fer)-L120-Lys(Flu)-L90-Lys(Flu)-L90-Lys(Flu)=Fer-(Lys(Fer)-L30)5-(L90-Lys(Flu))3. This extended conjugate was prepared by the same route as D19112: Boc-(Lys(2ClZ)-L30)5-(L90-Lys(Fmoc))3 was prepared on solid phase. The three Fmoc groups were removed with piperidine in NMP, and three carboxy fluoresceins introduced as in D19112. The intermediate product, NH2-(Lys(NH2)-L30)5-(L90-Lys(Flu))3 was cleaved of the resin and labeled with Ferulic acid at the N-terminal and 5 free lysine side chains, washed with 10% ethylenediamine in NMP, precipitated from TFA and HPLC purified.

D18146: ACim-(Lys(ACim)L30)5-(L90-Lys(Flu))3 was prepared on the same Lysine-Linker skeleton as D18126. Following cleavage from solid phase, the intermediate fluorescein labeled linker was dissolved in NMP and made basic with DIPEA. 4-amino-cinnamic acid, 0.1 M in NMP was activated with 0.9 equi.HATU and 3 equi DIPEA for 30 seconds, and added to the linker. The reaction was quenched after 2 min by addition of ethylenediamine to a final concentration of 10%. Following precipitation the product was purified by RP-HPLC.

D18074: Fer(Lys(Fer)-L30)5-Lys(NH2). this intermediate linker with 6 ferulic acids and a free lysine side chain amino group was prepared by solid phase chemistry, using a C terminal Boc-Lys(Fmoc) followed by alternating coupling with Boc-L30 linker and Boc-Lys(2ClZ). Following cleavage from resin, the intermediate product NH2(Lys(NH2)-L30)5-Lys(Fmoc) was labeled with ferulic acid in solution as described for D19112. In the final treatment with 10% ethylenediamine, the Fmoc group was also removed. This homo ferulic acid oligomer was used in the preparation of dextran conjugate D21008.

D18118: NH2-Cys-(L90Lys(Flu)) This intermediate trifluorescein linker was prepared directly on solid phase, using Boc-Lys(Fmoc) to introduce lysines, that following removal of the Fmoc were labeled with carboxy fluorescein. The N-termina cystein was introduced using Boc(S-p-methoxybenzyl) cysteine.

D18044: On solid phase Fer-(Tyr-L30)5-(L90-Lys(Flu))3 was prepared as D18126. N-Boc-O-2BrZ tyrosine was used to introduce the tyrosines. Following cleavage from the resin the product was HPLC purified.

D21008: Dex70 conjugate with D18074 and D18118. 10 nmol vinyl sulphone activated 70 kDa dextran in 140 microL water was mixed with further 200 microL water and 60 microL 0.8 M sodium hydrogen carbonate, pH 9.5. This mixture was used to dissolve 500 nmol freeze dried D18074. The reaction mixture was maintained at 40 C for 60 min, then further 500 nmol D18118 dissolved in 250 microL water was added to the reaction mixture together with further 50 microL 0.8M sodium hydrogen carbonate, pH 9.5. After additional 60 min reaction at 40 C, the reaction was stopped by addition of 70 microL 0.165 mM cystein in 0.8 M sodium hydrogen carbonate, pH 9.5. The conjugate was purified on superdex 200, using 10 mM CHES pH 9.0, 100 mM NaCl in 20% ethanol in water as eluent. This resulted in a first peak containing the conjugate, followed by unconjugated linkers. Based on a total recovery of 81% of fluorescien and ferulic acid, and assuming the same recovery rate (81%) for the dextran conjugate, a ratio of 111 ferulic acids and 83 fluoresceins per dextran was calculated, corresponding to (D18074)$_{18.5}$-Dex70-(D18118)$_{27.7}$.

D19059: On 0.1 g of MBHA resin with standard solid phase chemistry Boc-Lys(2ClZ)-Lys(2ClZ)-L$_{150}$-Lys(Fmoc) was prepared. The Fmoc protected Lysine side chain was deprotected with 20% piperidine in NMP (2×5 min) and subjected to labeling with 150 mg 2-4-dinitro-flourobenzene dissolved in 1.5 ml NMP 1.5 mL and 50 µL DIPEA for 2×20 min. The resin was treated with 20% piperidine in NMP, NMP and DCM.

The intermediate product was cleaved of the resin with TFA:TFMSA:thioanisol:m-cresol (6:2:1:1, 1.5 mL, for 1 h), precipitated with diethyl ether, resuspended in TFA, precipitated with diethyl ether, resuspended in NMP and again precipitated with diethyl ether. It was made basic with 100 µL DIPEA and dissolved directly in 0.5 mL 0.3 M Ferulic acid preactivated with 0.9 equi HATU and 2 equi DIPEA. After 10 min. the crude product was precipitated with diethyl ether, redissolved in 900 µL NMP and 100 µL ethylendiamine. After 2 min. the product was precipitated with diethyl ether. Resuspended in TFA, precipitated with diethyl ether, dissolved in 22% acetonitril in water (8.2 mL) and subjected to RP-HPLC purification.

Yield 8 µmol, MS found 3582 (M+Na). calc 3558.784 for Fer-Lys(Fer)-Lys(Fer)-$L_{150}$-Lys (DNP)

D19112: On 1 g of MBHA resin with standard solid phase chemistry Boc-Lys(2ClZ)-Lys(2ClZ)-$L_{150}$-Lys(Fmoc) was prepared. The Fmoc protected Lysine side chain was deprotected with 20% piperidine in NMP (2×5 min) and subjected to repeated carboxy fluorescein labeling (3 mL 0.2 M in NMP, preactivated for 2 min with 0.9 equi HATU, 1 equi DIPEA) 3×20 min. The resin was treated with 20% piperidine in NMP then washed with NMP, DCM and TFA. The intermediate product was cleaved of the resin with TFA:TFMSA:thioanisol:m-cresol (6:2:1:1, 3 mL, for 1 h), precipitated with diethyl ether, resuspended in TFA, precipitated with diethyl ether, resuspended in NMP and again precipitated with diethyl ether. It was made basic with 200 µL DIPEA and dissolved directly in. 2 mL 0.3 M Ferulic acid preactivated with 0.9 equi HATU and 2 equi DIPEA. After 10 min. the crude product was precipitated with diethyl ether, redissolved in 1350 µL NMP and 150 µL ethylendiamine was added. After 2 min. the product was precipitated with diethyl ether. Resuspended in TFA, precipitated with diethyl ether, dissolved in 25% acetonitril in water (24 mL) and subjected to RP-HPLC purification.

Yield 19 µmol, MS found 3749. calc 3750.998 for Fer-Lys(Fer)-Lys(Fer)-$L_{150}$-Lys (Flu)

D19185: D19185 was prepared analogously to D19112, by solid phase synthesis, followed by labelling with Ferulic acid in solution. MS found 4054

D19037: D19037 was prepared analogously to D19112, by solid phase synthesis, followed by labelling with Ferulic acid in solution. MS found 3447

D18126: On MBHA resin with standard solid phase chemistry Boc-(Lys(2ClZ)-$L_{30}$)$_5$$L_{90}$-Lys(Fmoc)-$L_{90}$Lys(Fmoc)-$L_{90}$ Lys(Fmoc)) was prepared. The Fmoc protected Lysine side chain was deprotected with 20% piperidine in NMP (2×5 min) and subjected to repeated carboxy fluorescein labeling (3 mL 0.2 M in NMP, preactivated for 2 min with 0.9 equi HATU, 1 equi DIPEA) 3×20 min. The resin was treated with 20% piperidine in NMP then washed with NMP, DCM and TFA. The intermediate product was cleaved of the resin with TFA:TFMSA:thioanisol:m-cresol (6:2:1:1, 3 mL, for 1 h), precipitated with diethyl ether, resuspended in TFA, precipitated with diethyl ether, resuspended in NMP and again precipitated with diethyl ether. It was made basic with 200 µL DIPEA and dissolved directly in 2 mL 0.3 M Ferulic acid preactivated with 0.9 equi HATU and 2 equi DIPEA. After 10 min. the crude product was precipitated with diethyl ether, redissolved in 1350 µL NMP and 150 µL ethylendiamine was added. After 2 min. the product was precipitated with diethyl ether. Resuspended in TFA, precipitated with diethyl ether, dissolved in 25% acetonitril in water (24 mL) and subjected to RP-HPLC purification.

Yield 2 µmol, MS found 10666,

Synthesis of Other Reporters of General Formula: Y-(Lys(Y))3-L150-Lys(Z).

Synthesis of Precursors:

NH2-(Lys(NH2))3-L150-Lys(Fmoc), (Pre4)

By Boc-solid phase chemistry on MBHA resin Boc-(Lys(2ClZ))3-L150-Lys(Fmoc)-Resin was prepared as previously disclosed. Cleavage from the resin for 1 hour with 6:2:1:1 TFA:TFMSA:m-cresol:thioanisol followed by diethyl ether precipitation gave crude NH2-(Lys(NH2))3-L150-Lys(Fmoc). The product was purified by three times dissolving in TFA, followed by diethyl ether precipitation and a final precipitation from NMP.

Fer-(Lys(Fer))3-L150-Lys(NH2), (Pre5)

NH2-(Lys(NH2))3-L150-Lys(Fmoc) prepared as described above on 1 gram of MBHA resin was dissolved in 750 microL MMP, made basic by addition of 100 microL DIPEA. To this solution was added 1 mL of 0.25 M HATU activated Ferulic acid. Following 10 min reaction 200 microL ethylenediamine was added and after 5 min reaction the crude product was isolated by precipitation with diethyl ether, immediately dissolved in TFA and precipitated with diethyl ether two times, and finally dissolved in 25% acetonitrile in water and RP-HPLC purified. 18 micromoles, 60 mg, were isolated and portioned into two micromole fractions and freeze dried.

Fer-(Lys(Fer))3-L150-Lys(7-Hydroxy-4-Methyl-Coumarine-3-Acetic Acid) (Reporter 6).

Fer-(Lys(Fer))3-L150-Lys(NH2), two micromoles, were dissolved in 100 microL NMP and 5 microL DIPEA. 2.3 mg 7-hydroxy-4-methyl-coumarine-3-acetic acid in 50 microL NMP was activated with 3.5 mg HATU and 3.5 microL DIPEA for 1 minute and added to the solution of Fer-(Lys(Fer))3-L150-Lys(NH2). Following 10 minutes reaction, the reaction mixture was quenched by addition of 20 microL ethylenediamine for 2 minutes and the product precipitated by addition of diethyl ether. It was dissolved in 200 microL TFA and precipitated with diethyl ether, followed by RP-HPLC purification. Yield 4 mg.

Fer-(Lys(Fer))3-L150-Lys(7-Amino-4-Methyl-Coumarine-3-Acetic Acid) (Reporter 7).

Fer-(Lys(Fer))3-L150-Lys(NH2), two micromoles, were dissolved in 100 microL NMP and 5 microL DIPEA. 2.3 mg 7-amino-4-methyl-coumarine-3-acetic acid in 50 microL NMP was activated with 3.5 mg HATU and 3.5 microL DIPEA for 1 minute and added to the solution of Fer-(Lys(Fer))3-L150-Lys(NH2). Following 10 minutes reaction, the reaction mixture was quenched by addition of 20 microL ethylenediamine for 2 minutes and the product precipitated by addition of diethyl ether. It was dissolved in 200 microL TFA and precipitated with diethyl ether, followed by RP-HPLC purification. Yield 4 mg.

Fer-(Lys(Fer))3-L150-Lys(7-Diethylamino-4-Methyl-Coumarine-3-Acetic Acid) (Reporter 8).

Fer-(Lys(Fer))3-L150-Lys(NH2), two micromoles, were dissolved in 100 microL NMP and 5 microL DIPEA. 2.9 mg 7-diethylamino-4-methyl-coumarine-3-acetic acid in 50 microL NMP was activated with 3.5 mg HATU and 3.5 microL DIPEA for 1 minute and added to the solution of Fer-(Lys(Fer))3-L150-Lys(NH2). Following 10 minutes reaction, the reaction mixture was quenched by addition of 20 microL ethylenediamine for 2 minutes and the product precipitated by addition of diethyl ether. It was dissolved in 200 microL TFA and precipitated with diethyl ether, followed by RP-HPLC purification. Yield 3 mg.

Fer-(Lys(Fer))3-L150-Lys(Naphtofluorescein) (Reporter 9)

Fer-(Lys(Fer))3-L150-Lys(NH2), two micromoles, were dissolved in 100 microL NMP and 5 microL DIPEA. 6 mg carboxy-naphtofluorescein in 50 microL NMP was activated with 3.5 mg HATU and 3.5 microL DIPEA for 1 minute and added to the solution of Fer-(Lys(Fer))3-L150-Lys(NH2). Following 10 minutes reaction, the reaction mixture was quenched by addition of 20 microL ethylenediamine for 2 minutes and the product precipitated by addition of diethyl ether. It was dissolved in 200 microL TFA and precipitated with diethyl ether, followed by RP-HPLC purification. Yield 5 mg.
Fer-(Lys(Fer))3-L150-Lys(Rhodamine 6G) (Reporter 10).

Fer-(Lys(Fer))3-L150-Lys(NH2), two micromoles, were dissolved in 100 microL NMP and 5 microL DIPEA. 5 mg Rhodamine 6 G-NHS ester was added. Following 10 minutes reaction, the reaction mixture was quenched by addition of 20 microL ethylenediamine for 2 minutes and the product precipitated by addition of diethyl ether. It was dissolved in 200 microL TFA and precipitated with diethyl ether, followed by RP-HPLC purification. Yield 2 mg.
Fer-(Lys(Fer))3-L150-Lys(TexasRedX) (Reporter 11).

Fer-(Lys(Fer))3-L150-Lys(NH2), two micromoles, were dissolved in 100 microL NMP and 5 microL DIPEA. 5 mg TexasRedX NHS-ester was added. Following 10 minutes reaction, the reaction mixture was quenched by addition of 20 microL ethylenediamine for 2 minutes and the product precipitated by addition of diethyl ether. It was dissolved in 200 microL TFA and precipitated with diethyl ether, followed by RP-HPLC purification. Yield 3 mg.

All reporters comprising a fluorescent or chromogenic label of the described above may be used both for forming deposits of the second substrate at target sites according to the invention and as stains for visualizing the deposits. Some non-limiting examples of use of selected reporters in both applications are described below in EXAMPLES 1-5.
Biding Agents
Goat-Anti-Mouse-Dex70-HRP (D18033/D18175)

13.7 nmol divinylsulphone were activated 70 kDA MW dextran and reacted with 602 nmol HRP were in 600 microL buffer (100 mM NaCl, 25 mM NaHCO$_3$, pH 9.5) for 3 h at 30 C. Then 41.1 nmol Goat-anti-Mouse F(ab)$_2$ antibody in 105 microL water was added, and the reaction was continued for additional 16 h. The reaction mixture was quenched by addition of 70 microL 0.165M cystein for 30 min and the product was purified on superdex 200 in 100 mM NaCl, 10 mM HEPES pH 7.2. The eluted product was a Dextran conjugate comprising Goat-anti-Mouse (GaM) and HRP (8 HRP and 1,3 antibody pr conjugate; ratio dex/GaM/HRP=1/1.1/7.5).
Anti-FITC-Dex70-HRP (D18058/D18144)

10 nmol divinylsulphone activated 70 kDA MW dextran and 440 nmol HRP were reacted in 400 microL buffer (100 mM NaCl, 25 mM NaHCO$_3$, pH 9.5) for 3 h at 30 C. Then, 30 nmol Anti-Mouse F(ab)$_2$ antibody in 80 microL water was added, and the reaction was continued for additional 90 min at 40 C. The reaction mixture was quenched by addition of 50 microL 0.165M cystein for 30 min and the product was purified on superdex 200 in 100 mM NaCl, 10 mM HEPES pH 7.2. The eluted product was a conjugate of Dextran with anti-FITC and HRP (9 HRP and 1.5. antibody per conjugate; Dex/anti-FITC/HRP Ratio=1/2/9).
Rabbit-Anti-FITC F(Ab')$_1$-HRP Conjugate (D19142/D19154)

Polyclonal rabbit-anti_FITC IgG antibody was digested with pepsin for 4 h at 37 C. and subjected to purification on superdex 200 to remove pepsin and Fc fragments.

The F(ab')$_2$ fragment was further dialysed against 5 mM EDTA in 0.2 M sodium phosphate, pH 6.0. The solution was concentrated with Amicon Ultra spin columns to a protein concentration of 25 g/L. To 6.0 mL of said solution (150 mg F(ab')$_2$) was added 487 microL 50 mg/mL DTT and 423 microL 56 mM 2-mercaptoethanol, both in water. The reaction mixture was gently stirred for 40 min at room temperature, and immediately after purified on PD-10 column with 5 mM EDTA in 0.2 M sodium phosphate, pH 6.0. 118 mg F(ab')$_1$ was recovered in 8.0 mL buffer.

HRP (Servac), 250 mg, was dissolved in 2.5 mL 0.15 m NaCL, 0.05M potassium phosphate pH 8 and dialysed against the same buffer. Following dialysis the enzyme solution was concentrated and adjusted to a concentration of 40 mg/mL. To 3.21 mL, 128.6 mg HRP solution was added 860 microL 15 mg/mL SMCC, and the reaction was allowed to proceed for 30 min in the dark at room temperature. The SMCC activated HRP enzyme was purified on PD-10 column with 0.15 m NaCL, 0.05M potassium phosphate pH 8. 126.9 mg were recovered in 7.9 mL.

To the 8.0 mL of F(ab')$_1$ was added 6.25 mL of the SMCC activated HRP solution, and the total volume was adjusted to 43.8 mL with 0.15 m NaCL, 0.05M potassium phosphate pH 8. The reaction between antibody fragment and enzyme was carried out for 210 min in the dark at room temperature. The reaction was then quenched by addition of 343 microL 25 mg/mL cysteamine in water for 15 min at room temperature, and the reaction mixture was stored in the cold over night awaiting purification. The sample was concentrated to 8 mL, and in 4 portions applied to a superdex 200 column and eluted with 150 mM NaCL, 50 mM Tris, pH 7.6. The product eluded in the first peak, followed by a peak of un-reacted antibody and enzyme. 100 mg of conjugate was isolated in several fractions. UV-measurements at 280 nm/403 nm showed antibody enzyme ration between 0.8 and 1.2.
Goat-Anti-Mouse F(Ab')$_1$-HRP (D19150/D19147)

Goat-anti-Mouse F(ab')$_1$-HRP was prepared as Rabbit-anti-FITC F(ab')$_1$-HRP, by reduction of F(ab')$_2$ with DTT and mercaptoethanol and coupling to SMCC activated HRP. As with Rabbit-anti-FITC F(ab')$_1$-HRP, 12 equivalents of SMCC was used for HRP activation and a 1:1 molar ration between F(ab')$_1$ and HRP was used.
Goat-Anti-Rabbit F(Ab')$_1$-HRP (AMM 279.168)

Goat-anti-Rabbit F(ab')$_1$-HRP was prepared as Rabbit-anti-FITC F(ab')$_1$-HRP, by reduction of F(ab')$_2$ with DTT and mercaptoethanol and coupling to SMCC activated HRP. As with Rabbit-anti-FITC F(ab')$_1$-HRP, 12 equivalents of SMCC was used for HRP activation and a 1:1 molar ration between F(ab')$_1$ and HRP was used.
Binding Agent Goat-Anti-Mouse F(Ab')$_1$-HRP Conjugate (D19150)

This was prepared by the same procedure as D19142 (with GaM instead of FITC).
Binding Agent Rabbit-Anti-DNP F(Ab')$_1$-HRP Conjugate (D19053)

This binding agent was prepared by the same procedure as D19142 using a polyclonal rabbit anti DNP antibody.
Binding Agent Rabbit-Anti-FITC F(Ab')$_1$-Alkaline Phosphatase Conjugate (D20036)

Rabbit-anti-FITC was pepsin digested and reduced to F(ab)$_1$ as described for D19142. 44.9 mg of the fragmented antibody in 4.23 mL buffer was used for the conjugation. Alkaline Phosphatase (Boehringer, MW 140.000) 56 mg in 2.8 mL buffer (25 mM borate, 200 mM NaCl, 5 mM MgCl2, 0.2 mM ZnCl2, pH 8.2) was reacted with 1.6 mg SMCC (12 equivalents relative to enzyme) dissolved in 107 microL DMSO for 25 min at room temperature in the dark. This activated enzyme solution was subjected to gel filtration using a buffer with 0.1 M TRIS, 0.2 M NaCl, 5 mM MgCl2, 0.2 mM ZnCl2, pH 8.2. 55.3 mg enzyme was isolated in a volume of 7 mL. The fragmented antibody and activated enzyme were immediately mixed together and further 2.47 mL 0.1 M TRIS, 0.2 M NaCl, 5 mM MgCl2, 0.2 mM ZnCl2, pH 8.2 was added. The mixture was allowed to react for 150 min at room temperature, and was then quenched by addition of 11.2 mg cysteamine for 15 min. The product was purified on a Superdex 200 column using 0.1 M TRISI, 5 mM MgCl2, 0.2 mM ZnCl2, pH 7.2, eluding as a single broad peak. Individual fractions assayed for AP activity and FITC binding in an IHC assay using D19150 to deposit reporter D19185, followed by the different fractions and finally Liquid Permanent red as chromogen. All major product containing fractions perform equally well and were pooled.

Binding Agent Goat Anti-Mouse Antibody Conjugated with Dex70 Conjugated with HRP (D20052)

11 nmol 70 kDA MW dextran was reacted with 484 nmol HRP in 316 microliters of buffer A (100 mM NaCl, 25 mM NaHCO$_3$, pH 9.5) for 3 h at 30 C. Thereafter 66 nmol Goat-anti-Mouse-F(ab)$_2$ in 169 microL water was added to the dextran-HRP conjugate and allowed to react for 1 h. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising Goat-anti-Mouse (GaM) and HRP. The use of a relatively short conjugation time, in combination with high molecular weight optimized purification allowed separating the final conjugate product into 15 fractions based on conjugate size. Measurements on individual product fractions, as well as fractions containing non-conjugated antibody and HRP, showed the conjugate recovery of 81%, corresponding to 8.91 nmol dextran. Collectively the conjugate fractions (fractions 7 to 22 of the eluate) contained 72.3 nmol HRP and 7.9 nmol antibody corresponding to 8.1 HRPs/dextran and 0.88 antibodies/dextran in average. Fractions 7-8 produced an initial peak, followed by a broad peak (fractions 9-17) that trailed off (fractions 18-22).

Goat Anti-Mouse Antibody Conjugated with Dex70 Conjugated with HRP (D20168)

This conjugate was produced in exactly the same way as D20052. To obtain a product with a uniform number of HRPs only fractions 9 and 10 were collected and pooled together.

Goat Anti-Mouse Antibody Conjugated with Dex-150 Conjugated with HRP (D20060)

This binding agent was prepared as D20052, though a larger molecular weight (150 kDa) dextran was used. During purification the vast majority of conjugate was eluded in a single peak in the first 4 fractions. Calculations showed 16.5 HRPs and 1.8 antibodies per dextran molecule in average.

Goat-Anti-Mouse Antibody Conjugated with Dex150 Conjugated with HRP (L348.121)

5.13 nmol 150 kDA MW dextran was reacted with 484 nmol HRP in 300 microliters of buffer, (100 mM NaCl, 25 mM NaHCO$_3$, pH 9.5) for 3 h at 40 C. Thereafter 66 nmol Goat-anti-mose F(ab)2 in 169 microL of water was added to the dextran-HRP conjugate and allowed to react for further 1 h at 40 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising Goat-anti-Mouse F(ab)2 and HRP. The product was divided into 3 fractions based on conjugate size: The first fractions (8-11) containing the largest conjugates, the trailing fractions with smaller conjugates, and unconjugated proteins. Measurements on individual product fractions, as well as fractions containing non-conjugated antibody and HRP, showed a total conjugate recovery of 87%. Assuming direct proportionality between incorporated HRP and Dextran showed that fractions 8-11 contained 20.6 HRPs and 2.32 antibodies per Dextran. fractions 10-11 contained 10.9 HRPs and 0.96 antibodies per Dextran. Only Fractions 8-11 were used for experiments.

This conjugate exemplifies how use of larger dextran conjugates allows incorporation of more HRPs.

Goat Anti-Rabbit Antibody Conjugated with Dex70 Conjugated with HRP (L348.111, Fractions 10-11.)

11 nmol 70 kDA MW dextran was reacted with 484 nmol HRP in 316 microliters of buffer A (100 mM NaCl, 25 mM NaHCO$_3$, pH 9.5) for 3 h at 40 C. Thereafter 44 nmol Goat-anti-Rabbit 196 microL water was added to the dextran-HRP conjugate and allowed to react for further 1 h at 40 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising Goat-anti-Rabbit (GaR) and HRP. The product was divided into 4 fractions based on conjugate size: The first two fraction containing product (Frac. 8-9) eluded as a first peak, presumably containing some cross linked conjugates, then followed by a broad shoulder that was divided into fractions 10-11 (homogeneous large conjugates) and fractions 12-21 (smaller variable conjugates) and finally unconjugated enzymes and antibodies in fractions 22-42. Measurements on individual product fractions, as well as fractions containing non-conjugated antibody and HRP, showed a total conjugate recovery of 87%. Assuming direct proportionality between incorporated HRP and Dextran showed that fractions 10-11 contained 10.9 HRPs and 0.96 antibodies per Dextran. Only these two fractions were used for experiments.

Anti-HER2-Antibody Conjugated with Dex70 Conjugated with HRP (D21100, Fractions 9-10)

4.6 nmol 70 kDA MW dextran was reacted with 202 nmol HRP in 125 microliters of buffer A (100 mM NaCl, 25 mM NaHCO$_3$, pH 9.5) for 3 h at 30 C. Thereafter 18 nmol antiHer2 in 489 microL of water was added to the dextran-HRP conjugate and the mixture was allowed to react for further 21 h at 30 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising antiHer2 and HRP. The product was divided into 4 fractions based on conjugate size: The first two fraction containing product (Frac. 7-8) eluded as a first peak, presumably containing some cross linked conjugates, then followed by a broad shoulder that was divided into fractions 9-10 (homogeneous large conjugates) and fractions 11-19 (smaller variable conjugates) and finally unconjugated enzymes and antibodies in fractions 20-41. Measurements on individual product fractions, as well as fractions containing non-conjugated antibody and HRP, showed a total conjugate recovery of 68%. Assuming direct proportionality between incorporated HRP and Dextran showed that fractions 9-10 contained 9.1 HRPs and 0.6 antibodies per Dextran. Only these two fractions were used for experiments.

antiFITC Antibody Conjugated with Dex70 Conjugated with HRP (AMM 353-022 fractions 8-11.)

11 nmol 70 kDA MW dextran was reacted with 484 nmol HRP in 316 microliters of buffer A (100 mM NaCl, 25 mM NaHCO$_3$, pH 9.5) for 3 h at 40 C. Thereafter 66 nmol antiFITC in 196 microL of water was added to the dextran-HRP conjugate and allowed to react for further 1 h at 40 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising antiFITC and HRP. The product was divided into 3 fractions based on conjugate size: The first fractions (8-11) containing product eluded as a first peak, then followed by a broad shoulder (smaller variable conjugates, frac. 12-27) and finally unconjugated enzymes and antibodies in fractions 28-45. Measurements on individual product fractions, as well as fractions containing non-conjugated antibody and HRP, showed a total conjugate recovery of 90%. Assuming direct proportionality between incorporated HRP and Dextran showed that fractions 10-11 contained 11.7 HRPs and 0.80 antibodies per Dextran. Only these two fractions were used for experiments.

Anti-HER2-Dextran70-HRP, (MAM 371-047)

Divinylsuphone activated dextran 70 (70 kDa), 11 nmol was reacted with 484 nmol HRP in 300 microL 160 mM NaCl and 40 mM sodium carbonate, pH 9.5, for three hours at 30 degrees. 210 microL corresponding to 7.7 nmol dextran, of the mixture was extracted, and reacted with 30.8 nmol monoclonal rabbit antiHER2 in 930 microL 100 mM NaCl for further 21 hours at 30 degrees. The reaction was stopped by addition of 114 microL 0.165 M cysteine, and the product purified on Sepharyl 300, with 100 mM NaCl, 10 mM HEPES pH 7.4 as eluent. 1.5 mL fractions were collected, and the concentration of antiHER2 and HRP assessed for each fraction.

When tested in a single molecule detection assay on HER2 positive cell lines, it was observed that the largest molecular weight first fractions (fraction 7-9) of the conjugate gave significantly fewer and somewhat larger dots than fractions 10-12 when diluted to same antiHER2 concentration. When the conjugate fractions were blocked with HER2 peptide and tested, fractions 7-9 gave more dots arising from unspecific binding than fractions 10-12.

This greater specificity and selectivity of fractions 10-12 we ascribe to large molecular weight dextran-aggregates in the first fractions with multiple dextrans cross linked via multiple antiHER2 antibodies. This is consistent with the stated separation characteristics of Sepharyl 300. For highly sensitive assays as described herein, fraction 11 was chosen. This was the central fraction of conjugate, with approximately equal amounts of conjugate in prior and following fraction. In combination with an overall coupling yield of 1.48 antibody and 8.95 HERs antibodies per dextran, we conclude that fraction 11 contains well defined 70 kDa dextran conjugates with said ratio of antibodies and HRPs.

All binding agents described above may be utilized in different steps of visualization procedures according to the invention. Some non-limiting examples of use of selected reporters in the procedures of the invention are described below in EXAMPLES 1-5.

Other Reagents
DAB chromogen solution (Dako K3465)
LPR chromogen solution (Dako K0640)
Haematoxilin counterstain (Dako S3301)
Wash buffer (Dako S3306)
Target retrieval solution (Dako S1699)

Example 1: Target Visualization Using DAB, Ferulic Acid and ACHCA as First Substrates As constant test material was used serial sections of pellets of formalin fixed paraffin embedded cell lines. The cell lines used were 0+, 1+ and 3+ control cell lines from Dako HercepTest™ embedded in a single paraffin block.

16 Slides with FFPE sections of blocks containing the cell lines, from now on referred to as "slides" were de paraffinized by emersion in xylene (2×5 min) followed by 96% ethanol (2×2 min) and 70% ethanol (2×2 min). The slides were washed with de ionized water and transferred to low pH target retrieval solution (Dako S1700). The slides were then heated to boiling in a microwave oven (approx 5 min) and then gently boiled for 10 min. The slides were allowed to cool for min 20 min before being transferred to wash buffer, Dako S 2343.

The slides were then stained on the Autostainer using the following protocol:
Peroxidase block, Dako S2023, 5 min
Wash
Primary antibody: 1 microgram/ml AntiHer2 antibody, clone DAK-HcT-2-DG44 in incubation media 1 for 10 min
Wash
Secondary antibody: Goat-anti-Rabbit-dextran70-HRP conjugate, L357.161 with on average 1.0 antibody and 11 HRPs per dextran conjugate prepared as previously disclosed. A concentration of 10 pM conjugate in incubation media 1 for 10 min was used. The concentration of primary and secondary antibody was chosen so as, when using the optimal cross linker DAB, to give one or a few 3-4 micron dots per cell in the 0+ cell line, several distinct or coalescent dots per cell in the 1+ cell line and a totally coalesced intense membrane stain in the 3+ cell line.
Wash
Reporter deposition: In all cases was used 5 microM D21067, Sin-Lys(Sin)-Lys(Sin)-L150-Lys(Flu) and 0.005% hydrogen peroxide (1.5 mM) in deposition media: 50 mM imidazole HCl pH 7.5, 0.1% Nonidet P40, 0.1%, benzalkonium chloride, 0.005% (1.5 mM) hydrogen peroxide, for five or ten min. These conditions were optimal using DAB as cross linker. The cross linkers tested were:
None, slide 1 (ten min) and slide 2 (5 min).
1 mg/ml (5.2 mM) ferulic acid, slide 3 (ten min) and slide 4 (5 min)
0.3 mg/ml (1.5 mM) ferulic acid, slide 5 (ten min) and slide 6 (5 min)
0.1 mg/ml (0.52 mM) ferulic acid, slide 7 (ten min) and slide 8 (5 min)
3 mg/ml (16 mM) alpha-cyano-4-hydroxy-cinnamic acid slide 9 (ten min) and slide 10 (5 min)
1 mg/ml (5.3 mM) alpha-cyano-4-hydroxy-cinnamic acid slide 11 (ten min) and slide 12 (5 min)
0.3 mg/ml (1.6 mM) alpha-cyano-4-hydroxy-cinnamic acid slide 13 (ten min) and slide 14 (5 min)
0.12 mg/ml (0.56 mM) DAB slide 15 (ten min) and slide 16 (5 min)
Three washes
Anti-FITC-AP: 10 min, 20 nM D20036 in incubation media 1
Three washes
LPR 10 min with Dako K0640
Wash
Haematoxylin (Dako S3301) diluted one part to three parts water, 5 min
Wash with water
Wash
The slides were desalted in water for 5 min dehydrated in 99.9% ethanol for 2 min and then film cover slipped on Tissue-Tek Film from Sakura.
The slides were inspected by microscopy.
Conditions of deposition reaction using different first substrates indicated above have been found to be optimal to obtain target staining as large dots (the largest possible) (see below discussion), however, they are exemplary and the reaction may be performed under other conditions which are discussed above (see Description).

Results:

Remarkably, there were observed no faintest red color in slides 1 and 2 which were incubated in the deposition media without the first substrate. Even the 3+ cell line was totally blank after 10 min. In contrast, under optimal conditions all three first substrates (termed hereafter "cross linkers") produced one or a few dots per cell in the 0+ cell line. This demonstrates the strong difference of in power of signal amplification by the present visualization system compared to the conventional CSA system.

With DAB as cross-linker, the 3+ cell line showed a complete broad membrane stain. The difference in staining between 5 and 10 min of deposition of the reporter was little and insignificant. The number of dots observed in the 0+ and 1+ cell lines was expected.

The optimal concentration of ferulic acid as cross-linker was found to be 1.5 mM. With this cross-linker the signal intensity increased dramatically correlating with an increase in duration of the deposition time from 5 to 10 minutes. Compared to the DAB-mediated deposition, after 5 min with ferulic acid-mediated deposition hardly any signals could be seen in the 0+ cell line, whereas after 10 min, there were as many dot as in corresponding DAB-stained slides and even larger dots were observed. The dots were, however, were much more diffuse, with a strong tendency to coalescence even in the 0+ cell line.

The optimal concentration of alpha-cyano-4-hydroxy-cinnamic acid as cross-linker was found to be around 5.3 mM. The dot size correlated with the time of deposition, in particular smaller dots were observed after 5 min of incubation compared to 10 min incubation. The membrane staining of the +3 cell line was dotted with very distinct dots of a smaller size compared to both DAB and ferulic acid-mediated staining. In most of cases the dots were coalescing into a crisp almost complete membrane stain. In the 0+ and 1+ cell lines it could likewise be observed that the dots were very distinct with little or no tendency to coalesce, probably due to their smaller size and more crisp appearance. Sometimes it required a closer inspection the slides to observe all dots, as both higher magnification and adjustment of focal plane were necessary.

Summary of the results of the stainings are given in the below table:

|  | DAB | Ferulic acid | ACHCA |
|---|---|---|---|
| Optimal amount | 0.14 mM | 1.5 mM | 5 mM |
| Optimal $H_2O_2$ amount | 1.5 mM | 0.9 mM | 0.6 mM |
| Optimal deposition time | 5-10 min | 10-15 min | 10-15 min |
| Optimal second substrate | Contains Fer or Sin | Contains Sin | Contains Fer |
| Dot diameter | 3-4 microns | 3-4 microns | 2-3 microns |

The relative large differences in reaction conditions were rather surprising, in particular, using 5 mM DAB tiny or no dots were produced and the noise staining was significant; using ACHCA in 0.14 mM, which was optimal for DAB, no dots were produces at all. Likewise, the preferences for the second substrate were different: ACHCA as cross linker produce only tiny dots (around 1 microns) with reporters comprising sinapinic acid, conversely Ferulic acid as cross linker performed better with reporters comprising sinapinc acid. The dot size increase was insignificant, if the time of the incubation was increased from 5 min to 10 min for DAB, and little for ACHCA, whereas hardly any dots were produced after 5 minutes incubation with Ferulic acid as cross linker.

All the cross-linkers, i.e. DAB, ACHCA and ferulic acid, may be used to produce both dotted and conventional homogeneous stains employing the amplification system described herein (or one described in WO2011/0476680 or WO2010/094283 and WO2010/094284 for Ferulic acid and DAB). ACHCA provides very crisp stains (both dotted and conventional) as well as DAB, however, ACHCA has a great advantage before DAB, that is solutions comprising the compound are clear and colorless compared to DAB, even when ACHCA is used at high concentrations for conventional staining. This provides for the produced stains have a color that is exclusively defined by the detectable label of the used reporter and, thus, facilitates analysis of the stained samples (by image analysis and under microscopic observation) providing expected results. Additionally, ACHCA compared to DAB is not toxic and its performance as the first substrate is less, if not at all, dependent on the amounts of a peroxide in the deposition solutions. Compared to ferulic acid as the first substrate, all type of stains obtained so far with ACHCA were crisper.

Example 2: New Colors for Target Staining in Histological Samples

As constant test material was used serial sections of pellets of formalin fixed paraffin embedded cell lines. The cell lines used were 0+, 1+ and 3+ control cell lines from Dako HercepTest™ embedded in a single paraffin block.

Slides with FFPE sections of blocks containing the cell lines, from now on referred to as "slides" were de paraffinized by emersion in xylene (2×5 min) followed by 96% ethanol (2×2 min) and 70% ethanol (2×2 min). The slides were washed with de ionized water and transferred to low pH target retrieval solution (Dako S1700). The slides were then heated to boiling in a microwave oven (approx 5 min) and then gently boiled for 10 min. The slides were allowed to cool for min 20 min before being transferred to wash buffer, Dako S 2343.

The slides were then stained on the Autostainer using the following protocol for fluorescent stains:

Peroxidase block, Dako S2023, 5 min
Wash
Primary antibody: antiHer2 antibody, clone DAK-HcT-2-DG44 1 microg/mL in—incubation media 1 for 20 min.
Wash
Secondary antibody: Goat-anti-Rabbi-Dextran70-HRP, 5 picomolar in incubation media 1 for 20 min.
Three washes
First Deposition mixture: 50 mM imidazole:HCl pH 6.8, 0.58 mM hydrogen peroxide, 5 mM ACHCA and 10 microM reporter for 10 min. The following reporters were used:
Fer-(Lys(Fer))3-L150-Lys(7-hydroxy-4-methyl-coumarine-3-acetic acid)
Fer-(Lys(Fer))3-L150-Lys(7-amino-4-methyl-coumarine-3-acetic acid)
Fer-(Lys(Fer))3-L150-Lys(carboxy-fluorescein)
Fer-(Lys(Fer))3-L150-Lys(TexasRedX)
Fer-Lys(Fer)-L150-Lys(Lissamine)

Three washes

The slides were desalted in de-ionized water and dehydrated in 99.9% ethanol and mounted with anti-fade fluorescence mounting media (Sakura), and viewed by fluorescence microscopy.

Results:

The reporters, Fer-(Lys(Fer))3-L150-Lys(7-hydroxy-4-methyl-coumarine-3-acetic acid) and Fer-(Lys(Fer))3-L150-Lys(7-amino-4-methyl-coumarine-3-acetic acid) produced small (around 2 microns) but distinct blue fluorescent dots, when viewed through the DAPI filter; more dots were observed in the +1 cell line than in the +0 cell line; in the +3 cell line the dots coalesced into complete membrane staining.

Fer-(Lys(Fer))3-L150-Lys(carboxy-fluorescein) produced large green fluorescent dots (around 3 microns in diameter), when viewed through the FITC filter. More dots were observed in the +1 cell line than in the +0 cell line, the dots coalesced into complete membrane staining in the +3 cell line.

Fer-(Lys(Fer))3-L150-Lys(TexasRedX) and Fer-Lys(Fer)3-L150-Lys(Lissamine) produced large (around 3 microns) red fluorescent dots, when viewed through the TexasRed filter. More dots were observed in the +1 cell line than in the +0 cell line; the dots coalesced into complete membrane staining on the +3 cell line.

For chromogenic stains the following protocol was used:
Peroxidase block, Dako S2023, 5 min
Wash
Primary antibody: antiHer2 antibody, clone DAK-HcT-2-DG44 1 microg/mL in incubation media 1 for 20 min.
Wash
Secondary antibody: Goat-anti-Rabbi-Dextran70-HRP, 5 picomolar in incubation media 1 for 20 min.
Three washes
First Deposition mixture: 50 mM imidazole:HCl pH 6.8, 0.58 mM hydrogen peroxide, 5 mM alpha-cyano-hydroxycinnamic acid and 10 microM Fer-(Lys(Fer))3-L150-Lys(carboxy-fluorescein) for 10 min.
Three washes
Tertiary antibody: 40 nM antiFITC-HRP in deposition media 1 for 10 min
Three washes
Second deposition mixture: 50 mM imidazole:HCl pH 6.8, 0.58 mM hydrogen peroxide, 5 mM alpha-cyano-hydroxycinnamic acid with 50 microM reporter. The following reporters were used:
Fer-(Lys(Fer))3-L150-Lys(carboxy-fluorescein)
Fer-(Lys(Fer))3-L150-Lys(carboxy-naphtofluoresein)
Fer-(Lys(Fer))3-L150-Lys(Rhodamine 6 G)
Fer-(Lys(Fer))3-L150-Lys(7-diethylamino-4-methyl-coumarine-3-acetic acid)
Fer-(Lys(Fer))3-L150-Lys(TexasRedX)
Fer-Lys(Fer)-L150-Lys(Lissamine)
Three washes
Haematoxilin 5 min.
Wash with water
The slides were desalted in water for 5 min dehydrated in 99.9% ethanol for 2 min and then film cover slipped on Tissue-Tek Film from Sakura and viewed by bright field microscopy.

All reporters produced colored dots, more in the +1 cell line than in the +0 cell line. In the +3 cell lines the dots coalesced into complete membranous stains. The color of the dots reflected the color of the reporter. Fer-(Lys(Fer))3-L150-Lys(7-diethylamino-4-methyl-coumarine-3-acetic acid) produced faint yellow dots, Fer-(Lys(Fer))3-L150-Lys(carboxy-fluorescein) produced brownish orange dots, Fer-(Lys(Fer))3-L150-Lys(Rhodamine 6 G) produced clear red dots, Fer-Lys(Fer)-L150-Lys(Lissamine) produced magenta dots, Fer-(Lys(Fer))3-L150-Lys(TexasRedX) produced purple dots and Fer-(Lys(Fer))3-L150-Lys(carboxy-naphtofluoresein) produced turquoise dots.

These examples illustrate the great utility and versatility of ACHCA as the first substrate in conjunction with diverse fluorescent and colored reporters. Control experiments with alpha-cyano-hydroxy-cinnamic acid alone without reporters did not produce any fluorescent or visible dots, which may be a case when DAB is used as cross-linker of reporter molecules. One reason for this is that ACHCA has a good solubility and is colorless in aqueous solutions, and it is possible to obtain a clear and well-defined color of the specific stain at target sites (as dots and homogeneous) that is exclusively dictated by the color of the reporter, and no background staining at all. This gives an additional advantage of the described system, especially when multiplexing and image analysis are used for staining and analysis of the staining results.

Example 3: Detection of Low Levels of Target in a Histological Sample

Detection of low levels of HER2 using MAM 371-0477, antiHER2-Dextran70-HRP, fraction 11.

As test material was used slides with FFPE sections, of cell line MDA 468. This cell line is often referred to as "true zero" as it has been considered void of HER2 expression using other techniques. The slides were de paraffinized by emersion in xylene (2×5 min) followed by 96% ethanol (2×2 min) and 70% ethanol (2×2 min).

The slides were washed with de ionized water and transferred to low pH target retrieval solution (Dako S1700). The slides were then heated to 97 degrees for 20 min in a PT-Link pretreatment module (Dako). The slides were allowed to cool to 65 degrees for min 20 min before being transferred to wash buffer, Dako S 2343.

The slides were then stained on the Autostainer using the following protocol:
Peroxidase block, Dako S2023, 3 min
Wash
Primary antibody: Slides 1-3 and 7-9 no primary antibody, slides 4-6 1 microg/mL antiHER2 in incubation media: 0.1% 4-aminoantipurine, 0.2% Procline 2%, BSA, 0.2% Casein, 2% PEG, 0.1% Tween20, 0.1 M NaCL, 10 mM HEPES, pH 7.2 (ABCPT-buffer), 20 min.
Wash
Secondary antibody: Slides 1-6 antiHER2-Dextran70-HRP, fraction 11, 500 pM in ABCPT-buffer, Slides 7-9 antiHER2-Dextran70-HRP, fraction 11, 500 pM+1 microg/mL HER2 peptide in ABCPT-buffer, 20 min.
Two washes
First Deposition mixture: 50 mM imidazole:HCl pH 6.8, 0.58 mM hydrogen peroxide, 5 mM alpha-cyano-hydroxycinnamic acid and 10 microM Fer-(Lys(Fer))3-L150-Lys(FITC), 10 min
Two washes
Tertiary antibody: 40 nM antiFITC-F(ab)1-Alkaline phosphatase in ABCPT-buffer, 10 min.
Wash
Liquid permanent red, Dako K0640, 10 min
Wash
Haematoxilin, 3 min
Wash with water
Wash
The slides were desalted in de-ionized water and dehydrated in 99.9% ethanol and mounted with film cover slipper (Sakura), and viewed by bright field microscopy. On all slides 2-3 micron red dots were observed. The slides were scanned on Scanscope (Aperio) and the images subjected to automated image analysis using "ISH-algorithm vs. 1.0" from Indica Labs. The algorithm was tuned to detect both red dots, as well as blue nuclei. Only dots that were located within 5 microns from a nucleus were counted. The results are summarized in the tables below:

| Slide | Dots  | cells | Dots/cell |
|-------|-------|-------|-----------|
| 1     | 24963 | 5155  | 4.84      |
| 2     | 17393 | 5585  | 3.11      |
| 3     | 15364 | 5297  | 2.90      |
| 4     | 9637  | 5978  | 1.61      |
| 5     | 11317 | 5189  | 2.18      |
| 6     | 8812  | 5484  | 1.60      |
| 7     | 1588  | 5740  | 0.28      |
| 8     | 1130  | 5372  | 0.21      |
| 9     | 1343  | 5557  | 0.24      |

| Slides | Average dots/cell |
|--------|-------------------|
| 1-3    | 3.62              |
| 4-6    | 1.80              |
| 7-9    | 0.24              |

These results clearly demonstrate that the MDA 468 cell line does express very low levels of HER2. The control experiments using anti-Her2 (slides 4-6) or HER2 peptide comprising the epitope (slides 7-9) added in the incubation media in order to block the binding of the first binding agent (antiHER2-Dextran70-HRP, fraction 11) to Her2 in the sample show that the binding between the first binding agent and the target is indeed specific.

The experiment also demonstrates that the colorless first substrate ACHCA has a great utility for the detection of low expression targets, where the signal has to be amplified to the extreme.

Example 4: Rapid and Sensitive IHC Staining of Different Biological Markers

As test material slides with FFPE sections of blocks containing arrays of different normal and deceased human tissue types ware used, (further referred as "slides").

The slides were deparaffinized by emersion in xylene (2×5 min) followed by 96% ethanol (2×2 min) and 70% ethanol (2×2 min). The slides were washed with deionized water and transferred to the low pH target retrieval solution (Dako S1700). The slides were then heated to 97 degrees for 20 min in a PT-Link pretreatment module (Dako). The slides were allowed to cool to 65 degrees for min 20 min before being transferred to wash buffer, Dako S 2343.

The slides were then stained on the Autostainer using the following protocol:

Peroxidase block, Dako S2023, 3 min
Wash
Primary antibody: RTUs from Dako, incubations either 3, 5 or 8 minutes (see below)
Wash
Secondary antibody: Goat-anti-Rabbit F(ab)1-HRP 30 nM and Goat-anti-Mouse 30 nM in incubation media 0.1% 4-aminoantipurine, 0.2% Procline 2%, BSA, 0.2% Casein, 2% PEG, 0.1% Tween20, 0.1 M NaCL, 10 mM HEPES, pH 7.2 (ABCPT-buffer), 3 min.
Two washes
First Deposition mixture: 50 mM imidazole:HCl pH 6.8, 0.58 mM hydrogen peroxide, 13 mM ACHCA and 3.5 microM Fer-(Lys(Fer))3-L150-Lys(FITC), 3 min
Two washes
Tertiary antibody: 50 nM antiFITC-F(ab)1-HRP in ABCPT-buffer, 3 min
Wash
Second deposition mixture, 50 mM imidazole:HCl pH 7.4, 5.8 mM hydrogen peroxide, 2.8 mM DAB, 3 min
Wash
Haematoxilin, 3 min
Wash with water
Wash The slides were desalted in deionized water and dehydrated in 99.9% ethanol and mounted with film cover slipper (Sakura), and viewed by bright field microscopy.

Results.

1. Pan Specific Cytokeratin, Dako IR053, Incubation Time 5 Min:

All known cytokeratin positive structures were stained. In kidney tissue both low and high expression sites were intensely stained. Very low expression liver tissue showed complete membrane staining.

2. Cytokeratin 18, Dako IR618, Incubation Time 8 Min:

All known cytokeratin 18 positive structures were stained. Very low expression liver tissue showed complete membrane staining.

3. AMACR, Dako IR060, 5 Min:

Colon moccus membranes were intensely stained, as was brain tissue. Remarkably colon smooth muscle showed multiple small grainy structures and non-deceased prostate showed considerable grainy staining.

4. CD 4, Dako IR649, 8 Min:

Low expression structures such as macrophages in tonsil germinal centers were stained, as well as very low expression Kupfer cells in liver.

5. Ki67, Dako IR626, 3 Min:

In all tissues types a few dividing individual cells stood clearly out as intensely stained. In growing tissues, tonsil and intestine, there was extensive staining, including low expression structures in tonsil epithelium.

Conclusion:

In all cases the recommended incubation time for the antibodies is 20 min, and with the exception of Ki67, more efficient high pH target is recommended for these RTU antibodies. These results demonstrate that milder tissue preserving target retrieval can be used in combination with short incubation times, yet still very intense stains are obtained using a 3-minute duration of all four (secondary antibody-HRP, deposition mixture tertiary antibody-HRP and DAB stain) essential incubations. Staining of targets in all cases looked as a very crisp conventional homogeneous stain without clear resolution into dots.

The example shows that ACHCA may also be used as a component of a staining system providing a conventional pattern of target staining (such as HRP-DAB based IHC conventional stain). This may be used when it is desired to stain the bulk of target and thereby visualize the cellular morphology.

Example 5: Small Conjugate Molecules as the Second Substrate

As discussed above, the amplification system described herein, like the amplification systems described in WO2011/

0476680 or WO2010/094283 and WO2010/094284, can utilize a huge number of conjugate molecules that can serve as reporters. Non-limiting examples of staining procedures utilizing some relatively large conjugates are described in examples 1-4 above. This example describes non-limiting cases of histological staining utilizing relatively small conjugate molecules as reporters. One advantage of using these smaller reporters for target staining is that smaller deposits are generated in both signal amplification systems utilizing DAB, ACHCA and Ferulic acid, and, correspondingly, targets in samples are visualized as smaller dots. The smaller conjugates are also functional under deposition conditions that provide conventional-type stains of target (i.e. of homogeneous non-dotted pattern).

Syntheses

The conjugates
Fer-Lys(Fer)-Lys(Fer)-R-alanine-Lys(Flu) (D21155)
Fer-Lys(Fer)-Lys(Fer)-gly-Lys(Flu) (D21154)
Fer-Lys(Fer)-Lys(Fer)-Lys(Flu) (D21152)
were prepared analogously to above described reporters using Boc solid phase chemistry. Briefly, MBHA resin was loaded with Boc-Lys(Fmoc) (a loading amount around 0.1 mmol/g resin). It was then subjected to coupling with Boc-L30-OH (five cycles for D19112 and D21150, two cycles for D20118, and a single cycle for D20086) or coupling with Boc-gly-OH (D21154), Boc-betaalanine-OH (D21155). No linker was coupled to D21152. In all cases this was followed by two cycles of coupling with Boc-Lys(2Cl—Z)—OH. The Fmoc protected Lysine side chain was deprotected with 20% piperidine in NMP (2×5 min) and subjected to repeated carboxy fluorescein labeling (0.2 M in NMP, preactivated for 2 min with 0.9 equi HATU, 1 equi DIPEA) 3×20 min. The resins was treated with 20% piperidine in NMP then washed with NMP, DCM and TFA.

The intermediate products were cleaved of the resin with TFA:TFMSA:thioanisol:m-cresol (6:2:1:1, 3 mL, for 1 h), precipitated with diethyl ether, re-suspended in TFA, precipitated with diethyl ether, re-suspended in NMP and again precipitated with diethyl ether to give oily intermediates. These were made basic with It was made basic with DIPEA and dissolved directly in 0.3 M Ferulic acid pre-activated with 0.9 equi HATU and 2 equi DIPEA. After 10 min. the crude product were precipitated with diethyl ether, re-dissolved in NMP and 10% ethylendiamine was added. After 2 min the products were precipitated with diethyl ether re-suspended in TFA, precipitated with diethyl ether dissolved in 25% acetonitril in water and subjected to RP-HPLC purification. MALDI-TOF mass spectroscopy was used to identify fractions with pure products. UV-VIS spectroscopy was used to determine concentration and yield, using a molar coefficient of extinction of 73.000 at 498 nm (fluorescein peak).

Using a synthesis as described above even smaller conjugates might be prepared by substituting Lysines with 2,3-Diamino-propioninc acid or similar smaller diamino acids in either one or all positions in the Z-Head and Y-Tail, and other non-amino acid structures.

Immunohistochemical Detection of her2 Using Conjugates D21155, D21154 and D21152

The performance with regard to the dot size was compared with the previously described reporters having homogeneous Y-Head:
Fer-Lys(Fer)-Lys(Fer)-L30-Lys(Flu) (D20086),
Fer-Lys(Fer)-Lys(Fer)-L60-Lys(Flu) (D20118), and
Fer-Lys(Fer)-Lys(Fer)-L150-Lys(Flu) (D19112),
and with a reporter having a heterogenic Y-Head:
Sin-Lys(Sin)-Tyr-L150-Lys(Flu) D21150.

Immunochemical staining was performed as described in the above examples.

The table below presents the results of staining of tested histological samples using DAB as the first substrate:

| Reporter | Linker Structure | Y-Head | Relative Dot size* |
|---|---|---|---|
| D19112 | L150 | Fer-Lys(Fer)-Lys(Fer)- | 3 |
| D20118 | L60 | Fer-Lys(Fer)-Lys(Fer)- | 2 |
| D20086 | L30 | Fer-Lys(Fer)-Lys(Fer)- | 2 |
| D21155 | B-alanine | Fer-Lys(Fer)-Lys(Fer)- | 2 |
| D21154 | Glycine | Fer-Lys(Fer)-Lys(Fer)- | 1 |
| D21152 | None | Fer-Lys(Fer)-Lys(Fer)- | 2. |
| D19185 | L150 | Fer-Lys(Fer)-Lys(Fer)-Lys(Fer) | 3 |
| D21047 | L150 | Sin-Lys(Sin)-Lys(Sin)- | 4 |
| D21028 | L150 | Sin-Lys(Sin)-Lys(Sin)-Lys(Sin) | 3 |
| D21150 | L150 | Sin-Lys(Sin)-Tyr- | 3 |

The relative dots size approximately corresponds to maximum dot diameter in microns under optimal conditions: High pH target retrieval of tissue, 10 microM reporter, 1.6 mM $H_2O_2$ and 0.28 mM DAB in precipitation reaction for 10 min at room temperature, reporter recognition for 10 min with 20 nM anti-FITC-AP, followed by 10 min LPR. The relative scores have been judged from several experiments under different conditions (target retrieval and reporter concentration) on different tissue samples and control cell lines and are qualitative.

Generally, all the reporters comprising a linker compound of different length (referring to the table, from "none" (i.e. L is the covalent bond) to at least 150 atoms when L is L150) and a diverse Y-Head performed well. However, the results shows that extended linkers may be more preferable when the dots of lager size (3-4 microns) are desirable, and reporters with short linkers when the dots are wanted to be smaller (1-2 microns).

If assume that the dots are essentially spherical, then a dot diameter corresponds to the cubed reporter efficiency, the reporter D21047 reproducibly outperformed any other reporter under all conditions tested by providing the largest dots.

Reporter D21154 with a glycine linker, produced smaller dots compared to similar reporters with the identical Z-Head and no (D21152) or the one carbon atom extended β-alanine linker (D21155).

Reporters with extended Z-heads (4 ferulic or sinapic acid derivatives) resulted in smaller dots than the analogues with 3 ferulic or sinapinic acid derivatives in the Z-head. The reason could be that 4 enzyme substrates in the Z-head may form deposits at a higher speed than those that comprise 3 enzyme substrates; a very efficient second substrate deposition may form deposits closer to the center of enzyme activity and thus the area covered by the deposit will be smaller, which is visualized as a dot of a smaller diameter.

The reporter D21150, with a simple di-substituted dipeptide Sin-Lys(Sin)-Tyr- as Z-Head performed well.

Using either 5 mM ACHCA or 1,5 Ferulic acid instead of DAB as the first substrate in the presence of 0.6-5.8 mM $H_2O_2$ all reporter produced dots as well, however, the dots were somewhat smaller (25-50%) (in case of ACHCA) or less sharp and weaker in color (in case of Ferulic acid), compared to the dots obtained with DAB.

The invention claimed is:
1. A method for detection of an immobilized target in a sample, wherein the target inherently comprises or is linked to an enzyme with oxidoreductase enzymatic activity, comprising incubating a sample comprising the target in an aqueous solution comprising:
- (i) a first substrate of said enzymatic activity and
- (ii) a second substrate of said enzymatic activity,
wherein the first substrate is alpha-cyano-4-hydroxycinnamic acid (ACHCA) and the second substrate is a conjugate molecule comprising one or more compounds capable of serving as substrates of said oxidoreductase enzymatic activity and a detectable label, and detecting the detectable label of the second substrate.

2. The method according to claim 1, wherein the aqueous solution comprises a peroxide compound.

3. The method according to claims 1 or 2, wherein the second substrate is a conjugate molecule of the formula 1:

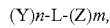

$(Y)n$-L-$(Z)m$, wherein
Y is a compound capable of serving as substrate of an enzyme with oxidoreductase activity;
Z is a detectable label;
L is a linker compound or a chemical bond,
wherein
n is an integer from 1 to 150, and
m is an integer from 1 to 150.

4. The method according to claim 3, wherein Y is a compound of the formula (II):

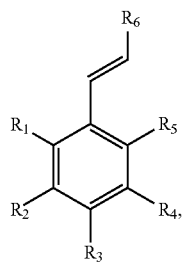

wherein
R1 is —H, —O—X, N(X)$_2$ or —S—X;
R2 is —H, —O—X, —N(X)2, or —S—X;
R3 is —H, —OH, —NH$_2$ or —SH;
R4 is —H, —O—X, —N(X)$_2$, or —S—X;
R5 is —H, —O—X, N(X)$_2$, or —S—X,
R6 is —CON(X)$_2$ or CO—X, wherein
H is hydrogen;
O is oxygen;
S is sulphur;
N is nitrogen; and
X is H, alkyl or aryl.

5. The method of claim 4, wherein the conjugate comprises at least two compounds Y of the formula (II).

6. The method according to claim 1, wherein the conjugate comprises one or more residues of ferulic acid, caffeic acid, sinappinic acid, or 4-amino cinnamic acid.

7. The method according to claim 1, wherein the detectable label is a fluorescent, luminescent, chromogenic, or radioactive substance.

8. The method according to claim 1, wherein the amount of alpha-cyano-4-hydroxycinnamic acid (ACHCA) is in the range from around 0.15 mM to around 50 mM.

9. The method according to claim 1, wherein the target is linked to an enzyme with oxidoreductase activity via an agent.

10. The method according to claim 9, wherein the agent is a target specific binding agent or an agent that is capable of specifically binding to a substance that is linked or associated with the target.

11. The method according to claim 10, comprising
   a) Incubating the sample supposedly comprising the target with one or more binding agents, wherein at least one of the binding agents is the target specific binding agent and at least one of the binding agents comprises an enzyme with oxidoreductase activity before incubating the sample in the aqueous solution;
   b) Incubating the sample (a) in an aqueous solution according to any of the claims 1 or 2-8;
   c) Detecting in the sample (b) deposits of the conjugate molecule comprising one or more compounds that are capable of serving as substrates of said enzymatic activity and a detectable label.

12. The method according to claim 11, wherein at least one of the binding agents is an antibody.

13. The method according to claim 12, wherein said at least one of the binding agents comprises a first binding agent and a second binding agent, and the first binding agent is the (Fab)$_1$ fragment of a primary polyclonal antibody comprising one moiety of a peroxidase or phenoloxidase.

14. The method according to claim 12, wherein said at least one of the binding agents comprises a first binding agent and a second binding agent, and the second binding agent is (Fab)$_1$ fragment of a secondary polyclonal antibody comprising one moiety of a peroxidase or phenoloxidase.

15. The method according to claim 1, wherein the sample is a biological sample comprising cells.

* * * * *